United States Patent [19]
Wheeler, deceased et al.

[11] Patent Number: 5,335,675
[45] Date of Patent: Aug. 9, 1994

[54] STRESS-SOFTENED ELASTOMERIC FILMS, ARTICLES, AND METHOD AND APPARATUS FOR MAKING SUCH FILMS AND ARTICLES

[75] Inventors: Robert G. Wheeler, deceased, late of Greenbank, Wash., by Helen J. Wheeler, legal representative; William D. Hawley, Angier, N.C.

[73] Assignee: Family Health International, Durham, N.C.

[21] Appl. No.: 775,783

[22] Filed: Oct. 11, 1991

Related U.S. Application Data

[60] Continuation-in-part of Ser. No. 726,984, Jul. 8, 1991, which is a continuation-in-part of Ser. No. 568,426, Aug. 16, 1990, Pat. No. 5,036,863, which is a division of Ser. No. 271,884, Nov. 15, 1988, Pat. No. 4,961,416.

[51] Int. Cl.$^5$ .................. A61F 6/02; A61B 19/00; A01N 51/00
[52] U.S. Cl. .................. 128/842; 128/849; 514/157
[58] Field of Search ............ 128/842, 844, 918, 849; 604/347–353; 514/157, 169; 528/361

[56] References Cited

U.S. PATENT DOCUMENTS

| | | |
|---|---|---|
| Re. 32,983 | 7/1989 | Levy . |
| D. 253,009 | 9/1979 | Okamoto . |
| 1,113,561 | 10/1914 | Jorgenson . |
| 2,285,981 | 6/1942 | Johns . |
| 2,410,460 | 11/1946 | Robinson . |
| 2,433,538 | 12/1947 | Warner . |
| 2,484,356 | 10/1949 | Ribeiro et al. . |
| 2,488,938 | 9/1950 | Wayne . |
| 2,577,345 | 12/1951 | McEwen . |
| 2,586,674 | 2/1952 | Lonne . |
| 3,037,508 | 6/1962 | Friedman . |
| 3,149,017 | 9/1964 | Ehririch et al. . |
| 3,157,724 | 11/1964 | Salyer et al. . |
| 3,247,857 | 4/1966 | Kanbar . |
| 3,295,145 | 1/1967 | Erickson . |
| 3,559,651 | 2/1971 | Moss . |
| 3,588,997 | 6/1971 | Field . |
| 3,631,857 | 1/1972 | Maddison . |
| 3,733,383 | 5/1973 | Bunney . |
| 3,759,254 | 9/1973 | Clark . |
| 3,992,766 | 11/1976 | Field . |
| 4,004,591 | 1/1977 | Freimark . |
| 4,009,717 | 3/1977 | Allen . |
| 4,022,213 | 10/1977 | Stein . |

(List continued on next page.)

FOREIGN PATENT DOCUMENTS

| | | |
|---|---|---|
| 0147072 | 7/1985 | European Pat. Off. . |
| 2020280 | 11/1971 | Fed. Rep. of Germany . |
| 2349361 | 4/1975 | Fed. Rep. of Germany . |
| 2085323 | 12/1971 | France . |
| 058743 | 10/1984 | Japan . |
| 63-281965 | 11/1988 | Japan . |
| 1595711 | 8/1981 | United Kingdom . |

OTHER PUBLICATIONS

"Stress Softening in Elastomer Blends," *J. Appl. Poly. Sci.*, 13, 1309–1318 (1969).

(List continued on next page.)

*Primary Examiner*—Michael A. Brown
*Attorney, Agent, or Firm*—Steven J. Hultquist

[57] ABSTRACT

A stress-softened thermoplastic elastomeric (TPE) film which has been subjected to tensional deformation comprising at least uniaxial strain, and having improved textural and thermal transmissivity characteristics, as compared to a native, unstretched material. Such stress-softened thermoplastic elastomeric film may be employed in a wide variety of articles, including condoms, finger cots, tubular bandages, and the like. Condoms comprising such stress-softened TPE film are described, including condoms having a main sheath comprising stress-softened and non-stress-softened areas in a pattern or other predetermined arrangement. A variety of methods and apparatus for forming stress-softened tubular articles of thermoplastic elastomeric film is disclosed.

14 Claims, 13 Drawing Sheets

U.S. PATENT DOCUMENTS

| | | |
|---|---|---|
| 4,031,214 | 6/1977 | Easterbrook ................... 514/157 |
| 4,232,675 | 11/1980 | Meldahl . |
| 4,241,828 | 12/1980 | Bourdelle et al. . |
| 4,275,812 | 6/1981 | Poncy . |
| 4,354,494 | 10/1982 | Hogan . |
| 4,432,357 | 2/1984 | Pomeranz . |
| 4,446,860 | 5/1984 | Gutnick . |
| 4,475,910 | 10/1984 | Conway et al. . |
| 4,484,918 | 11/1984 | Omley . |
| 4,546,029 | 10/1985 | Cancio et al. . |
| 4,576,156 | 3/1986 | Dyke . |
| 4,603,174 | 7/1986 | Okada . |
| 4,626,250 | 12/1986 | Schneider . |
| 4,735,621 | 4/1988 | Hessel . |
| 4,781,709 | 11/1988 | Grubman . |
| 4,794,929 | 1/1989 | Robichaud . |
| 4,795,425 | 1/1989 | Pugh . |
| 4,798,600 | 1/1989 | Meadows . |
| 4,805,604 | 2/1989 | Spery . |
| 4,833,172 | 5/1989 | Schwarz . |
| 4,855,169 | 8/1989 | McGlothlin et al. . |
| 4,867,937 | 9/1989 | Li et al. . |
| 4,955,392 | 9/1990 | Sorkin . |
| 4,964,416 | 10/1990 | Foldesy et al. . |
| 5,096,896 | 3/1992 | Graham ........................... 514/157 |

OTHER PUBLICATIONS

Estes, G. M., et al., "Infrared Studies of Segmented Polyurethane Elastomers. II. Infrared Dichrosim," *Macromolecules*, vol. 4, No. 4, Jul.–Aug. 1971, pp. 452–457.

Cowie, G. M. G., et al., "Effective Casting Solvent on the Stress-Hardening and Stress-Softening Characteristics of Kraton-G 1650 Copolymer Films," *J. Macromol. Sci.–Phys.*, B16(4), 611–623 (1979).

Payne, A. R., et al., "Mechanical Properties of High Density Cellular Urethanes," *J. Elastoplastics*, vol. 5 (Jul. 1973) pp. 161–177.

Handbook of Thermoplast Elastomers, Second Edition, Walker, B. M., Ed., Van Nostrand Reinhold Co., New York, 1988, pp. 15–16.

Godofsky, Y. K., et al., "Thermodynamics of the Deformation of Segmented Polyurethane With Various Hard Block Contents. II. Stress Softening and Mechanical Hysteresis," *Colloid Polym. Sci.* 267:414–420 (1989).

Kawabata, S. et al., Applications of the New Thermal Tests 'Thermolabo' to the Evaluation of the Clothing Comfort, in Objective Measurement:Applications to Product Designe and Process Control, Kawabata, S. et al., Eds. the Textile Machinery Society of Japan, 1985.

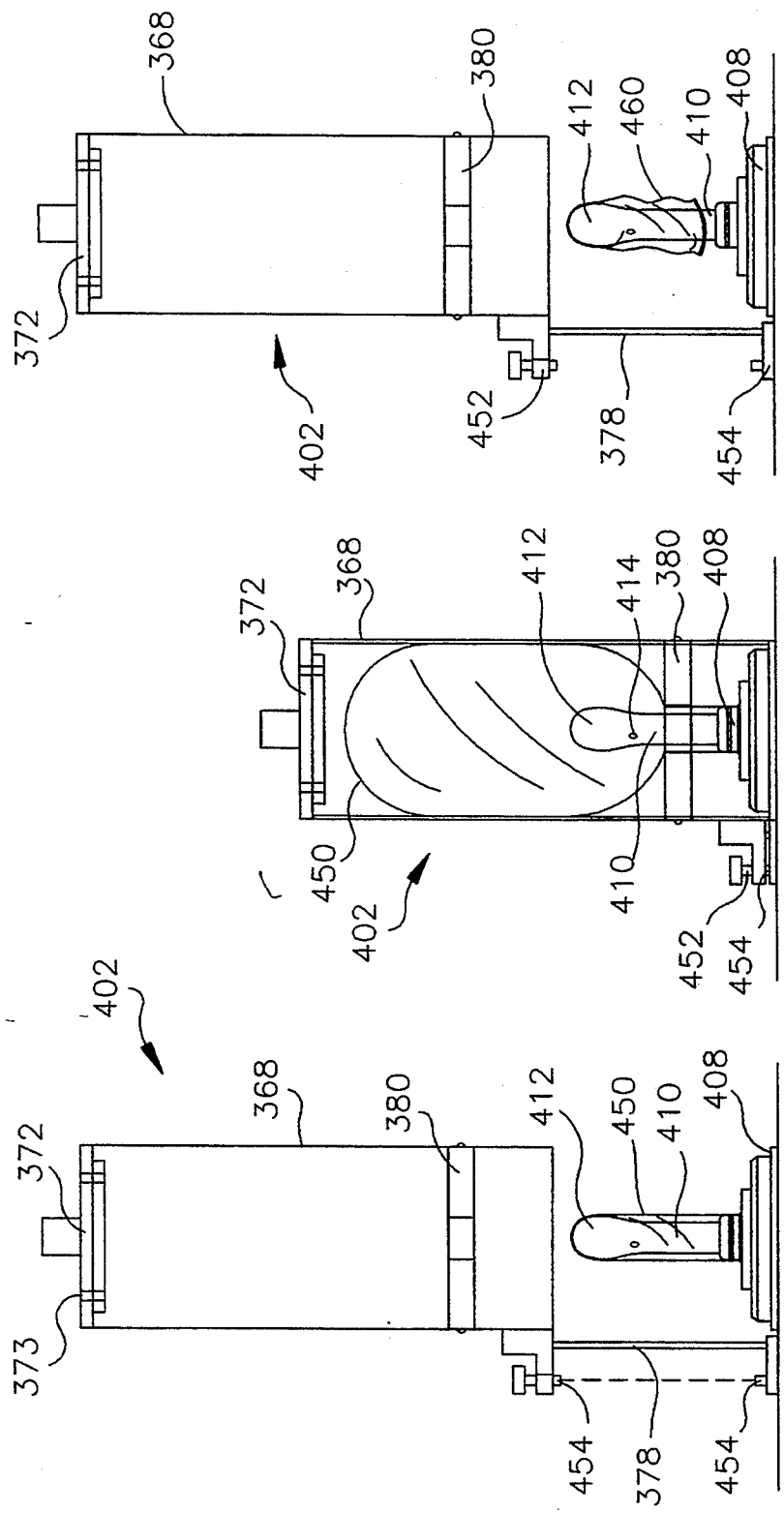

STRESS-SOFTENED ELASTOMERIC FILMS, ARTICLES, AND METHOD AND APPARATUS FOR MAKING SUCH FILMS AND ARTICLES

CROSS-REFERENCE TO RELATED APPLICATIONS

This application is a continuation-in-part of U.S. application No. 07/726,984 filed Jul. 8, 1991 in the name of Robert G. Wheeler, which in turn is continuation-in-part of U.S. Application No. 07/568,426 filed Aug. 16, 1990 in the name of Robert G. Wheeler and issued Aug. 5, 1991 as U.S. Pat. No. 5,036,863 which in turn is a division of U.S. application Ser. No. 07/271,884, filed Nov. 15, 1988 in the names of Robin G. Foldesy and Robert G. Wheeler, and issued Oct. 23, 1990 to Robert G. Wheeler as U.S. Pat. No. 4,961,416.

BACKGROUND OF THE INVENTION

1. Field of The Invention

This invention relates to stress softening of elastomeric films to improve the physical properties thereof, to articles comprising stress-softened elastomeric film, and to apparatus and methods for making stress-softened films and articles therefrom.

2. Background of The Related Art

Elastomeric films have been widely employed in the fabrication of elastic prophylactic articles, including gloves, condoms, finger cots, tubular bandages, and the like. Currently, these articles are primarily produced from a latex material via a dipping process in which an appropriately-shaped mold is dipped into a bath of the latex material, so that upon withdrawal, the mold is coated with a thin layer of the latex material. The thickness of the latex coating on the mold is dependent on the viscosity of the latex, and the speed of extracting the mold from the latex bath.

In respect of prophylactic articles, and specifically condoms, the recent spread of AIDS in the general population and the corresponding resurgence of condom usage in sexual activity has focused effort on improving the strength and reliability characteristics of condoms, and of achieving improvements in manufacturing processes and economics to further combat the spread of sexually transmitted diseases generally, and AIDS particularly, as well as to provide a safe and reliable contraceptive means.

U.S. Pat. No. 4,576,156 issued Mar. 18, 1986 to Manfred F. Dyke discloses a condom formed of a thermoplastic polyurethane material, having a generally cylindrical configuration with an open proximal end and a closed distal end. The disclosed condom has a thickness of from about 0.01 millimeters, or less, to about 0.25 millimeters. The thermoplastic polyurethane employed to form the condom is disclosed as having: an average Shore A hardness of from about 50 to about 90; a tensile stress, at 100% of elongation, between about 300 and 1,000 psi; and a tensile stress at 300% elongation, between about 800 and 3,000 psi. Suitable thermoplastic polyurethane species for manufacturing the condom include those set out at column 2, line 55 to column 3, line 10 of the Dyke patent, with polyether- or polyester-based urethane elastomers said to be preferred. In the manufacture of the thermoplastic polyurethane condom disclosed in the Dyke patent, a film of the polyurethane material, e.g., in the form of a 6-inch square, is heated to a temperature high enough to soften the polymer but low enough to avoid thermal degradation, preferably in a clamping frame, and at a temperature of about 400°–500° F. The heated film then is brought into contact with a preformed mandril to cause the film to assume the shape of the mandril, preferably with application of a vacuum to the system in order to bring about uniformity in wall thickness (column 3, lines 47–50 of the patent).

The film and condom article of U.S. Pat. No. 4,576,156 suffer from a number of deficiencies, which limit their utility. The film disclosed in such patent is heated to 400°–500° F., as necessary to soften the polyurethane-based thermoplastic elastomer without degrading the film (column 3, lines 36–41). Such temperatures will disrupt (melt) the small crystallites in the polyurethane film which make it elastomeric. This permits the disclosed "forming operations" to be carried out. Upon cooling, these crystallites reform, but on a microscopic basis, the film is at least predominantly isotropic (column 4, line 3). Thus, the strength achieved by orienting (extruding) the film during its original manufacture is lost. Second, the vacuum forming technique disclosed in this patent is used to "ensure . . . a pinhole free device" (column 3, lines 50–52). The tip of the vacuum formed film could develop pinholes after contact with the forming mandril. Holes in such area of the film would be sealed by surrounding "softened" polymer in contact with or adhering to the mandril, and the final vacuum forming could still be effected. There is no evidence in this patent for a "substantially uniform thickness" as identified at column 4, line 54 of the patent, and such alleged uniformity of thickness is contrary to what reasonably would be anticipated from the mode of fabrication employed for forming the disclosed condom article. The thickest portion should be the tip, and the thinnest portion should be the region where the hemispherical end of the condom meets the cylindrical sheath thereof. The heated fabrication described in this patent is fundamentally different in procedure and result from room temperature fabrication. The deformation effected by the mandril and vacuum causes the film to conform to the mandril. Thus, based on the method of fabrication disclosed in the patent, the resulting product article would appear to be characterized by substantial variation in film thickness from along the cylindrical sheath to the distal end of the condom.

U.S. Pat. No. 4,735,621 to L. Hessel discloses a tubular protective condom-like device comprising a flexible, thin-walled tube that may be formed of polyurethane. The tube is closed at one end and has at its opposite, open end, a collar-shaped, outwardly extending portion with means for radially stretching the open end. In one disclosed embodiment, the device has a first outwardly extending ring-shaped means adapted for radially extending the open end, and a second outwardly extending ring-shaped means that is adapted for radially extending the closed end. The second ring-shaped means thus secures or maintains the device in the vagina in manner similar to a diaphragm. The inner diameter of the device is sufficiently large to permit movement of a penis during coital contact.

U.S. Pat. No. 4,603,174 issued Jul. 29, 1986 to T. Okada, et al for "STRETCHED POLYPROPYLENE FILM", describes a stretched polypropylene film with allegedly excellent see-through characteristics, which is obtained without degrading the inherent properties or film-forming character of the polypropylene resin. The film is formed from a melt of a polypropylene resin containing a specific alpha-olefin and/or vinyl cycloalkane, and then stretched in at least one direction. The olefin and vinyl cycloalkane materials are described in the paragraph bridging columns 1 and 2 of the patent. The stretching techniques are described at column 2, lines 55-60 as employing conventional industrial methods, e.g., roll stretching, tenter stretching, and tubular stretching, in at least one direction, at a stretch ratio of 1.2 to 100 times in terms of the area stretch ratio.

In the paragraph bridging columns 2 and 3 of the patent, the benefits of stretching are described:

"Needless to say, a stretched film having excellent seethrough characteristics without optical nonuniformity can be obtained by stretching polypropylene resin sheet used in this invention. It has also been ascertained that as an incidental effect, the polypropylene resin sheet has better stretchability than conventional polypropylene resins. Specifically, the present inventors observe the reduction of the stretching stress and the decrease of the film breakage phenomenon during stretching."

Example I of the patent describes the polypropylene sheet being stretched by a tenter-type consecutive biaxial stretching device to four times in the machine direction at 145° C. and subsequently to ten times in the transverse direction at 160°, and then heat-treating at 145° C. to obtain a biaxially stretched film having a thickness of about 20 microns.

U.S. Pat. No. 3,637,579 issued Dec. 14, 1971 to C. J. Heffelfinger for "UNIDIRECTIONALLY ORIENTED FILM STRUCTURE OF POLYETHYLENE TEREPHTHALATE", describes a substantially unidirectionally-oriented polyethylene terephthalate film which among other characteristics has at least 50% elongation at break in the direction transverse to the direction of predominant orientation. The molecular orientation of the film is predominantly uniaxial by stretching at least four times the original dimension of the film in the direction of stretch. The film has a tensile strength of preferably at least 50,000 psi in the direction of stretching, and at least 50% elongation in the direction transverse to the stretching.

The patent discloses that stretching a film of polyethylene terephthalate is desirable from the standpoint of greatly increasing the tensile strength of the film in the direction of stretching. Stretch ratios of from slightly greater than one-fold to about five-fold are described (column 2, lines 68-70). In the sentence bridging columns 2 and 3 of the patent, it is disclosed that film stretching is desirable, by virtue of the fact that a film stretched two-fold possesses a modulus of 460,000 psi, whereas a film stretched five-fold possesses a modulus of about 1,800,000 psi. A film stretch ratio greater than five-fold is said to result in the failure of the film structure by fibrillation "of such an extensive nature as to destroy completely the useful structural integrity and unitary structure of the film" (column 3, lines 8-11). The unidirectionally stretched film is said to have an unexpected and totally surprising pneumatic impact strength (column 4, lines 15-16).

U.S. Pat. No. 3,733,383 issued May 15, 1973 to J. B. Bunney, et al, for "DEFORMATION OF POLYMERIC MATERIALS", describes a process for reducing the cross-sectional area of an article of an orientable thermoplastic polymeric material by drawing the article at a temperature below its melting point through a die of smaller cross-sectional area than that of the article. The deforming surface of the die is well lubricated and the molecular orientation of at least that part of the article to which drawing tension is applied, is such that the tensile strength of the article exceeds the drawing tension. The term "article" is defined at column 1, lines 52-57 as excluding articles having a cross-sectional area less than 0.01 square inch and whose largest external dimension is less than 0.05 inch. At column 2, lines 48-50, the patent refers to relaxation of extruded thermoplastic materials, due to hydrostatic extrusion effects. The process described in the patent is said to reduce the extent of such relaxation. At column 4, lines 34-42, the patent, in referring to deformation ratios applicable to extrusion of thermoplastics, states that:

"[T]hese ratios may also be related to the degree of molecular orientation in the product, and, since this has a marked effect on certain physical properties of the products, in particular their moduli, it follows that the use of our process can enable extruded and/or drawn articles (other than those of dimensions previously excluded) to be produced having moduli higher than those previously attainable. Thus a further aspect of our invention resides in such products as novel articles."

At column 1, lines 1-36, the patent discloses various X-ray diffraction patterns which are said to indicate very high degrees of molecular orientation, which in turn is said to be the reason for increased modulus in products of the invention.

U.S. Pat. No. 3,157,724 issued Nov. 17, 1964 to I.O. Salyer, et al, for "PRODUCTION OF HIGH STRENGTH ORIENTED ETHYLENE/VINYL ACETATE COPOLYMER FILM", describes the orientation of a film of high molecular weight ethylene/vinyl acetate. The orienting process is carried out at elevated temperatures which are generally above 25° C., but considerably below the melting point of the polymer. The copolymer is stretched at a rate of 50% to 5,000% per minute, and is stretched almost to the breaking elongation of the copolymer (e.g., 70%-90% of break) under conditions suitable for effecting and maintaining orientation. The oriented ethylene/vinyl acetate film of the invention is said to be remarkably improved in tensile and impact strengths, as well as uninitiated tear strength.

U.S. Pat. No. 3,247,857 issued Apr. 26, 1966 to M. S. Kanbar for "DENTAL FLOSS", describes a dental floss made of "exceptionally soft material, the floss having a smooth surface and a high tensile strength whereby the teeth and gums may be cleaned efficiently and without injury thereto" (column 1, lines 8-12). This improved dental floss is formed by loosely twisting a tape of an oriented polymer, such as a polyethylene or polyamide, into a helix forming a small compressible tube (column 1, lines 35-38). The starting material may be smooth film formed from an extruded polymer such as "Saran", polyethylene, polyesters, or polyamides, at a melt extruded film thickness of approximately 0.00015 inch. This film is slit into a tape of approximately 1 inch width, or alternatively, the film is extruded from a die in the desired tape width. The tape is stretched by passage through rolls comprising feed rolls and drawing rolls operating at different speeds, so that the tape is stretched therebetween. Stretching of the tape is said to orient the molecular structure of the film and thereby increase its tensile strength. The drawing may be hot drawing or cold drawing. The tape is stretched to approximately three times its initial length to produce a ribbon whose width is about one-half that of the original tape and about half as thick. The patent notes that after this treatment, "[t]he ribbon is much stronger than the stretched tape and is very soft" (column 2, lines 4–5). The ribbon then is twisted approximately 1–3 turns per inch to produce a floss having the desired character.

U.S. Reissue Pat. No. 32,983 reissued Jul. 11, 1989, to S. B. Levy, for "BALLOON AND MANUFACTURE THEREOF", discloses a polymeric balloon suitable for use in a balloon catheter system. The patent describes forming the balloon at a temperature of preferably 84° C.–99° C. by drawing a polymeric, preferably a polyethylene terephthalate homopolyester, tubing having an internal diameter which preferably is about one-half the outer diameter, to a length which is approximately three-fold to six-fold the original length. Thereafter the drawn tubing is expanded to an inner diameter which is preferably six-fold to eight-fold and an outer diameter which is preferably about three-fold to four-fold times the original inner and outer diameter, respectively. The balloon has a burst pressure of at least 200 psi and a radial expansion beyond nominal inflated diameter of less than 5% at 200 psi. The tubing material has an intrinsic viscosity of 0.8 to 1.1, and is formed by conventional extrusion techniques from PET homopolyester resin. The tubing is expanded in a confining apparatus shown in FIG. 1 of the patent, by means of a fluid such as nitrogen gas. The patent does not describe any hardness, or modulus, characteristics being changed as a result of the tubing expansion to form the balloon.

U.S. Pat. No. 3,304,353 issued Feb. 14, 1967 to A. Harautuneian for "METHOD OF CATHETER MANUFACTURE", describes a method of manufacturing balloon-type catheters constructed "entirely from plastic materials devoid of possible irritants such as rubber compounding or curing agents, all in a manner such that the balloon constitutes, in effect, a terminally integrated surface continuity of the tube of the necessary properties for sustained inflation" (column 1, lines 33–39). The patent at column 1, lines 47–51 describes illustrative balloon materials of construction as including elastomeric grades of polyurethane such as Goodrich "Estane" or Mobay Chemical "Texin". More particularly, the balloon layer is formed of a poly(esterurethane) of elastic grade and having a 300% stretch modulus within about the 600 to 1200 psi range. The catheter comprises a tube with a main passage and a second passage having a hole in its outer wall communicating with the exterior. The opening is covered with a coating of a water soluble partitioning material. Thereafter, the coating is covered with a thermoplastic balloon layer. Subsequently, in use, liquid injected through the second passage functions to dissolve the partitioning coating to establish fluid communication with the balloon layer, so that the balloon can be inflated to the desired extent. The poly(ester-urethane) layer is applied at thickness of from about 0.003 to about 0.008 inch by dipping the tube in poly(ester-urethane) resin dissolved in a suitable solvent such as THF, dimethyl formamide, or an 80-20 solution of THF and cyclohexane.

U.S. Pat. No. 4,833,172 issued May 23, 1989 to R. A. Schwartz, et al, for "STRETCHED MICROPOROUS MATERIAL", describes a method for producing stretched microporous material. A sheet is formed from a mixture comprising essentially linear ultra-high molecular weight polyolefin, e.g., polyethylene having an intrinsic viscosity of at least about 18 deciliters/gram, polypropylene having an intrinsic viscosity of at least about 6 deciliters/gram, or a mixture thereof, together with finely divided particulate substantially water-insoluble siliceous filler, and a processing plasticizer which is a liquid at room temperature. The processing plasticizer is substantially removed from the sheet to form a precursor microporous material, and the precursor microporous material is stretched in at least one stretching direction to at least one stretch ratio of at least about 1.5. This produces stretched microporous material which is dimensionally stable at room temperature, and has a stretch ratio in the stretching direction of at least about 1.5. The matrix of the stretched microporous material comprises (i) regions of stretched molecularly oriented ultra-high molecular weight polyolefin distributed throughout the matrix of the stretched material, (ii) filler distributed throughout the matrix of the stretched material, and (iii) a network of interconnecting pores communicating throughout the stretched microporous material. The patent at column 10, lines 25–48 discusses uniaxial stretching as well as biaxial stretching.

U.S. Pat. No. 4,867,937 issued Sep. 19, 1989 to H-M Li, et al, for "PROCESS FOR PRODUCING HIGH MODULUS FILM", describes a two-step process for increasing the modulus of a film in one or both directions. A thermoplastic film is drawn in at least one direction in a medium with a temperature of between about 10° C. above the glass transition temperature and 40° C. below the melting temperature, at a draw ratio of between 1.05 and 5.5, and is drawn in the same at least one direction in a medium having a temperature between about 5° C. and 35° C. below the melting temperature, at a draw ratio of between about 1.05 and 2.5. The films may be formed of materials such as those illustratively mentioned at column 2, lines 36–44 of the patent. The film-forming polymers are heated into a melt and then extruded through a nozzle or a die slit to form a film which then is cast on a cooling drum and solidified. The cast film is drawn a first time in either the longitudinal and/or transverse directions through a medium such as air at the requisite temperature, in which the drawing increases the tensile modulus of the film in the directions(s) of draw, followed by a second drawing step which induces substantial increase in the tensile modulus in at least one direction, thereby providing a 20%–40% improvement in the tensile modulus in the longitudinal and/or transverse direction.

U.S. Pat. No. 4,855,169 issued Aug. 8, 1989 to M. W. McGlothlin, et al, for "PROPHYLACTIC SHEATH WITH AUGMENTED BORDER", describes a prophylactic sheath fabricated from an elastic polymer material which is augmented along the border at the open end with a resilient material having a 100% tensile modulus substantially lower, preferably lower by at least 75%, than the modulus of the sheath material. Such provision is said to facilitate rolling of the edge and stretching of the sheath for purposes of application, without compromising the high degree of sensitivity in terms of heat and sensation transmission associated with the thin-walled sheath. The prophylactic may suitably be formed of thermoplastic elastomer materials, such as polyurethane, or block copolymer thermoplastic elastomer materials. The condom is described as being made by dip molding of a form or mandrel, and applying the augmented border in the form of a ring or band to the open end of the sheath, either removably or permanently. Bonding of the border element is achieved by self-curing, adhesives, or other conventional techniques such as fusing by heat or solvents. The border may be formed of a closed cell foam or solid elastomer. A wide variety of bands and rings are described as embodiments of the invention, together with a number of methods of forming same. The materials of construction of the augmented border are illustratively set forth at column 7, lines 23–42, and include various block copolymers such as Kraton ® copolymers and polyurethanes, with foam polyurethanes being most preferred. In the paragraph bridging columns 8 and 9 of the patent, it is stated that "[t]he polyurethane used for the sheath will be one which combines high strength with a high degree of softness." The tensile strength is at least about 6,000 psi. The softness, expressed as Shore A hardness, preferably ranges from about 50 to about 90, most preferably from about 60 to about 80. The sheath thickness is generally less than about 1.4 mils, and preferably is from about 0.4 to about 1.4 mils, and the 100% tensile modulus is at least about 200 psi.

U.S. Pat. No. 4,817,593 issued Apr. 4, 1989 to R. A. Taller, et al, for "PROCESS FOR PREPARATION OF POLYURETHANE CONDOMS", describes a dipping method for making polyurethane condoms, using a solvent solution of a polyurethane polymer or prepolymer which is the reaction product of a polyisocyanate with at least one long chain polyol having an average molecular weight of from about 500 to about 5,000 and a hydroxy number of about 225 to about 22.4, with an NCO/OH ratio of from about 0.95/1 to about 1.1/1. The condoms of this patent have a 100% tensile modulus of less than about 150 psi, and a thickness of between about 1.5 and about 4.0 mils. The polyurethane polymers used in the condom have a Shore A durometer hardness of about 35 to 60 (column 5, lines 4–5). The patent in the paragraph bridging columns 4 and 5 thereof describes the polyurethane polymers employed in the condom as having hard segments and the degree of cross-linking as being balanced within the ranges of approximately 14% to 25% hard segments and approximately 5,000 to 30,000 molecular weight per cross-link ($M_c$). The patent describes the advantages of low modulus materials of construction employed in the disclosed condom. Chemical cross-linking and physical cross-linking are employed in the polymer to reduce crystallization to yield the desired low modulus (column 5, lines 28–47).

U.S. Pat. No. 4,808,174 issued Feb. 28, 1989 to R. Sorkin for "CONDOM OF PLASTIC MATERIAL", discloses a condom of plastic material, preferably selected from the class which includes polyethylene, polypropylene, and vinyl materials. The condom also includes a pubic shield integral with it which is thicker than the material along the tubular length of the condom, with an adhesive preferably being applied to the pubic shield for attachment during coitus. The condom is described as being formed with a preferably translucent, and relatively thin plastic material in the range of about 0.03 millimeters. The patent discloses to reinforce the condom with fibrous material such as elongate strands of fine diameter fibers. The plastic shield is a circular disk of about 5 inches diameter and is of integral construction with the condom. There is no disclosure in the patent of strength or modulus properties of the materials of construction employed in the disclosed condom.

U.S. Pat. No. 4,881,553 issued Nov. 21, 1989 to R. A. Grossman for "MESH REINFORCED CONDOM", describes a condom which comprises a latex sheath having a reinforcing elastic mesh embedded in the walls of the sheath, with the elasticity of the mesh being about equal to or less than the elasticity of the latex sheath. The mesh may be coextensive with the length of the sheath or may be embedded in only the upper one-half or upper one-third end of the sheath. Column 2, lines 13–16 of the patent describes the mesh elasticity as being on the order of about 5% to 75% less than the elasticity of the condom walls. The mesh is stated to be formed from "an elastic thread such as natural rubber thread, or thread formed of synthetic rubber, silicone elastomer, or a fiber/polymer blend such as cotton/rubber. The wall of the condom disclosed in this patent is approximately 0.02–0.09 millimeters in thickness. The patent at column 3, lines 10–14 discloses that "when the reinforcing mesh is made from a flat sheet of thin plastic film, the projections 16 can be either embossed on the plastic film or formed by flaps of the film between slits 22."

U.S. Pat. No. 4,964,416 issued to Robert G. Wheeler discloses a variety of condoms which are amenable to construction from thermoplastic elastomeric materials including polyurethane materials, polyester elastomers, polyether block amides, etc.

In general, the use of synthetic elastomeric materials afford substantial advantages over latex as materials of construction for prophylactic articles. The strength and tensile modulus of polyurethane elastomers are about 3 times those of latex, an advantage that is also found to a greater or lesser extent in other thermoplastic elastomer materials, especially block copolymers comprising alternating hard and soft segments. In addition, thermoplastic elastomeric materials can be employed to form prophylactic articles of equivalent strength at substantially reduced thicknesses, relative to corresponding latex rubber articles. Further, synthetic thermoplastic elastomer materials display much greater chemical inertness to lubricants, spermicides, and the like, to which latex rubber may be susceptible to degradation or attack, particularly when these materials are petroleum-based in character.

A major deficiency of such thermoplastic elastomeric materials, however, is their stiffness and relatively high modulus character, and their lack of high elasticity, relative to latex rubber materials. In particular, the soft, supple, highly flexible character of latex rubber films, and their smooth, textural characteristics (referred to as "hand") generally are not matched by films of thermoplastic elastomeric materials.

*Handbook of Thermoplastic Elastomers*, Second Edition, B. M. Walker, et al (Van Nostrand Reinhold Company, 1988), pages 15 and 16, discusses the morphology of styrenic block copolymers, and shows changes in morphology of an A-B-A block copolymer, as a function of composition, so that with increasing content of A, the morphology changes from (1) A spheres in B continuous phase at low concentration, to (2) A cylinders in the B continuous matrix, followed by (3) A,B lamellae, with still further increasing A content producing (4) B cylinders in continuous A matrix, and finally (5) B spheres in continuous A matrix. The text states that these block copolymers, particularly those with a continuous polystyrene phase, show obvious stress softening, i.e., when the polymer is stretched to an elongation below its ultimate elongation, allowed to retract, and is then restretched, it appears much softer during the second extension than during the first. This feature is described as being similar to the so-called "Mullins effect" in conventional reinforced vulcanizates, and appears to be caused by the rupture of the continuous polystyrene phase during stretching to yield discrete domains.

Other references relating to softening of thermoplastic elastomeric films by application of stress followed by relaxation of same include: "Thermodynamics of The Deformation of Segmented Polyurethanes With Various Hard Block Contents. (II. Stress Softening and Mechanical Hysteresis)," Godovsky, U. K., et al, Colloid Polym. Sci., Vol. 267, No. 5, pages 414–420 (1989)) (thermodynamics of stress-softening and hysteresis in polybutadiene polyurethanes, and adverse impact on industrial application of polyurethanes by stress-softening and hysteresis losses); "Effect of Casting Solvent on the Stress-Hardening and Stress-Softened Characteristics of Kraton-G 1650 Copolymer Films," Cowie, J. M. G., et al, J. Macromol. Sci., Vol. B 16, No. 4, pages 611–623 (1979) (stress softening of Kraton-G cast from N-heptane, and subjected to repeated stress cycles); "Mechanical Properties of High-Density Cellular Urethanes," Payne A. R., et al, J. Elastoplastics, Vol. 5 (July 1973), pages 161–177 (hysteresis and stress softening of urethanes is recoverable up to temperatures of 170° C.); "Infrared Studies of Segmented Polyurethane Elastomers (II. Infrared Dichroism)," Estes, G. M., et al, Macromolecules, Vol. 4, No. 4, pages 452–457 (1971) (stress hysteresis of urethane domains of polyether- or polyester-polyurethanes); and "Stress Softening in Elastomer Blends," Meluch, W. C., Journal of Appl. Poly. Sci., Vol. 13, pages 1309–1318 (1969) (stress softening of ternary elastomeric system of natural rubber, nitrile rubber, and brominated butyl rubber (Hycar ®2202)).

It is important in understanding the above-described references and the field of the invention to distinguish between the useful stress softening of films, condoms, diaphragms, gloves, and other articles of thermoplastic elastomers, on the one hand, and the strengthening and stabilizing of films and filaments of semicrystalline thermoplastics, on the other hand. Distinctions can also be made between stress-softening and the heat-stretching of thermoset polyurethane filaments, e.g., those commercialized under the trademark Spandex ®.

Most of the work reported on stress-softening points out the substantially permanent set that occurs in the stressed material. Indeed, stress softening is used as an explanation of what happens when a thermoplastic elastomeric article is subjected to stress, undergoing an undesirable deformation and becoming permanently deformed. This limits the utility of such articles. The art has not recognized the benefits of stress softening, and in fact this phenomenon has heretofore been considered troublesome.

The stress-softening of TPE films differs from the stretching of Spandex ® yarns during manufacture. The polyurethane dopes (solutions of polyurethanes) are spun into filaments by dry (evaporation of solvent) or wet (coagulation of solution in a bath) processes. The polyurethane filaments then are subjected to stretching and heating to cause further reaction and setting. The resulting yarns are stable (to hot water during dyeing, for example, and to laundering). Without such treatment, such yarns would undergo permanent deformation (elastic bands in garments would become loose, for example). The tensile modulus, however, increases. This is not stress-softening.

Accordingly, it is an object of the present invention to provide thermoplastic elastomeric films which are stress-softened in character and amenable to usage in a wide variety of articles comprising such films.

It is another object of the present invention to provide articles comprising films of the foregoing type, as well as a method of making same.

It is yet another object of the present invention to provide an improved condom article formed of a thermoplastic elastomeric film material, which is stress-softened in character.

It is a still further object of the present invention to provide a method and apparatus for making such stress-softened thermoplastic elastomeric films and articles.

Other objects and advantages will be more fully apparent from the ensuing disclosure and appended claims.

SUMMARY OF THE INVENTION

The present invention relates broadly to stress-softened thermoplastic elastomeric films, and articles comprising such films, particularly condoms and similar articles. The invention also relates to a method of stress-softening of thermoplastic elastomeric film, and to a method and apparatus for forming condom articles comprising stress-softened thermoplastic elastomeric film.

As used herein, a "thermoplastic elastomeric film" is a film formed of a polymeric material which is (1) thermoplastic in character, i.e., which is softenable and flowable or otherwise permanently deformable by elevated temperature conditions at and above its melting point (as distinct from cross-linked or other non-thermoplastic polymeric materials which are not flowable or deformable by sufficient elevated temperature conditions, but rather are subject to decomposition, degradation, or chemical reaction at increasing temperature levels and do not have a determinable melting point), and (2) elastic in character, with respect to stretching of the material under application of tensional forces thereto.

In a specific aspect, the present invention relates to a stress-softened thermoplastic elastomeric film, having at least one of the following characteristics:

(i) a shear stiffness value of less than 2.5 gf/cm degree;

(ii) a tensile energy value of at least 1.0 gf/cm/cm$^2$;

(iii) an extensibility, at 50 gf/cm load, of at least 4.0%;

(iv) a dry heat loss value of at least 16.5 watts/m$^2$/° C.;

(v) a wet heat loss value of at least 22.0 watts/m$^2$/° C.; and (vi) a $Q_{max}$ value of less than 12.25 watts/m$^2$/° C.

A stress-softened thermoplastic elastomeric film of the above-described type may also be characterized by at least one of the following characteristics:

(i) a film thickness of less than 100 micrometers, with the film having been reduced in thickness by at least 10% from its original film thickness by tensional stretching of the film, preferably tensional stretching comprising strain which is at least uniaxial, and most preferably is at least biaxial, in orientation;

(ii) an elastic modulus at 20% elongation which is at least 15% lower than the elastic modulus at 20% elongation of a corresponding film of the aforementioned original film thickness, which has not been subjected to such tensional stretching (denoted hereinafter as "native film"); and (iii) a break ratio defined by $$\frac{(\% \text{ elongation at break})_{stress\text{-}softened\,film}}{(\% \text{ elongation at break})_{native\,film}},$$

which is less than 0.9 in value

The stress-softened thermoplastic elastomeric film of the invention preferably is stretchable and is at least partially elastic in character, i.e., it possesses a stretching regime within which a tensionally stretched length of the film will recover to near its original length when the tensional force is discontinued, preferably with the length of the film being within 20%, and most preferably within 15%, of the original film length (before application of the tensional force thereto).

The "elastic modulus at 20% elongation" refers to the elastic modulus measured at 20% elongation of a sample of the thermoplastic elastomeric film.

In a specific aspect, the stress-softened thermoplastic elastomeric film of the present invention may have at least one of the following preferred characteristics:

(i) a shear stiffness value of from 0.5 to 2.5 gf/cm degree;
(ii) a tensile energy value of from 1 to 3 $gf/cm/cm^2$;
(iii) an extensibility at 50 gf/cm load of 4–12%;
(iv) a dry heat loss value of 16.5 to 20.0 $watts/m^2/°C$;
(v) a wet heat loss value of 22 to 25 $watts/m^2/°C$; and
(vi) a $Q_{max}$ value of from 10 to 12.25 $watts/m^2/°C$.

The aforementioned shear stiffness value, tensile energy value, extensibility at 50 gf/cm load, dry heat value, wet heat loss value, and $Q_{max}$ value are the values determined by specific tests hereinafter more fully described.

The stress-softened thermoplastic elastomeric film of the invention may be formed of any suitable thermoplastic elastomeric material, but preferably is a film formed of a polymer comprising (i) hydrocarbonaceous chain moieties constituting relatively softer segments of the polymer, and (ii) relatively harder segments of the polymer. The hydrocarbonaceous chain moieties constituting the relatively softer segments of the polymer may be derived from any suitable linking moieties, e.g., polymerizable monomer precursor(s), such as olefins, including monoolefins and polyolefins, as well as hydrocarbylene chain segments, optionally substituted by heteroatoms, including alkylene chain segments, ether moieties, ester linking groups, etc. The relatively harder segments of the polymer may in turn be formed by any suitable moiety such as styrenic repeating units, amide blocks, acrylic functional groups, aromatic-containing repeating units, etc. Particularly preferred thermoplastic elastomers include polyether-based polyurethanes and polyester-based polyurethanes, as well as multi-block rubber-based copolymers.

As used herein, the term "stress-softened thermoplastic elastomeric film" refers to a thermoplastic elastomeric film which has been subjected to tensional stretching and then relaxed. Preferably, such stretching comprises at least uniaxial tensional stretching, and preferably at least biaxial tensional stretching, which, following relaxation of the stretched film is softened, e.g., has a reduced elastic modulus. For example, in respect of the tubular articles described hereinafter as having condom utility, which comprise a cylindrical sheath portion of a thermoplastic elastomeric film material, and which have a closed distal end, such an article may be longitudinally tensionally stretched, contemporaneously with radial stretching (expansion) of the article, by interior pressurization thereof. Preferably, the stress-softened film is a film of a suitable elastomer which has been tensionally stretched and then relaxed, such that it possesses the physical properties described hereinabove (including the shear stiffness, tensile energy, extensibility, dry heat loss, wet heat loss, and $Q_{max}$ values, as quantitatively specified hereinabove.

In an article aspect, the present invention relates to a condom including a main sheath comprising a stress-softened thermoplastic elastomeric film.

In a preferred condom of such type, the stress-softened thermoplastic elastomeric film has been stress-softened by biaxial stretching comprising longitudinal extension of the main sheath under the application of tensional force, concurrently with radial expansion of the main sheath, as for example by fluid pressure expansion of the main sheath in the radial direction, as hereinafter more fully described.

In another aspect, the present invention relates to a condom comprising a generally tubular main sheath which is comprised of stress-softened thermoplastic elastomeric film portions and non-stress-softened thermoplastic elastomeric film portions.

In a specific embodiment of a condom of such type, the condom comprises a generally tubular main sheath with a longitudinal axis, comprising longitudinally spaced-apart stress-softened main sheath portions alternating with non-stress-softened main sheath portions, e.g., with the non-stress-softened main sheath portions being in the shape of longitudinally spaced-apart circumferential bands along the main sheath of the condom.

In another specific embodiment of a condom of such type, the condom comprises a generally tubular main sheath with a longitudinal axis, and is characterized by a frontal burst test ratio value of from about 1.1 to about 1.8.

Another aspect of the invention relates to a method of stress-softening a thermoplastic elastomeric film, comprising tensionally stretching the film by applying thereto a strain which is at least uniaxial in orientation to reduce the thickness of the film by at least 10%, wherein the original thickness of the film is less than 100 micrometers, and such that the film subsequent to such tensional stretching is characterized by: (i) an elastic modulus at 20% elongation which is at least 15% lower than the elastic modulus at 20% elongation of a corresponding film of the original thickness which has not been subjected to the tensional stretching ("native film"); and (ii) at least one of the aforementioned shear stiffness, tensile energy, extensibility, dry heat loss, wet heat loss, and $Q_{max}$ values, as numerically specified hereinabove.

Another method aspect of the invention relates to a method of making a condom, comprising:
  forming a tubular sheath of a thermoplastic elastomeric material, the tubular sheath having a closed distal end and an open proximal end;
  axially stretching the tubular sheath on a mandril to effect elongation thereof and place the tubular sheath under axial tension in such elongation state;

expanding the sheath radially, contemporaneously with the imposition of the axial stretching elongation state, such as by imposition of a pressure differential, e.g., pressurizing the interior of the sheath with a fluid at suitable pressure; and discontinuing the radial expansion and axial stretching of the tubular sheath, to yield a stress-softened tubular sheath.

The foregoing method may be carried out with the tubular sheath being axially stretched and radially expanded within a confining cavity, to ensure the symmetric character of the resulting condom comprising the stress-softened thermoplastic elastomer film.

In another aspect, wherein a condom comprising axially alternating stress-softened portions and non-stress-softened portions is formed, the tubular sheath may be disposed on a hollow mandril, with retaining bands being positioned over the exterior surface of the condom at axially spaced-apart intervals. The mandril may be porous over its surface area covered by the tubular sheath, and be joined to a source of fluid.

Pressurized fluid is introduced into the interior of the mandril and employed to expand the portions of the sheath between the retaining bands, and to expand the sheath at the distal end thereof, followed by cessation of such pressurization, to yield the condom comprising stress-softened regions separated by non-stress-softened band-shaped portions. The condom produced by this method has a generally soft character, but the non-stress-softened band-shaped portions, being less flexible than the stress-softened portions of the sheath, afford a means of retaining the condom on the penis of a wearer, and also of restraining the disengagement of the condom from the penis during detumescence, by virtue of the circumferentially compressive effect of such band areas on the penis of the wearer, during and subsequent to use of the condom. Such non-stress-softened band areas also serve to prevent leakage of ejaculate from the condom, and contact with the coital fluids of the other coital partner, such as may result in infection by sexually transmitted diseases.

Still another aspect of the invention relates to a method of forming a condom, by the steps comprising:

providing a cavity mold comprising a first cavity-defining mold half-section, including a cavity, and a second planar mold half-section, the first and second mold half-sections being engageable with one another for face-to-face mating of the mold half-sections;

disposing superposed layers of thermoplastic elastomeric film in abutting relationship to one another, with the superposed sheets of thermoplastic elastomeric film clamped between the mold half-sections; and imposing a pressure differential on the abutting superposed sheets, so that they are transversely displaced and translated into bearing contact with interior surfaces of the cavity defined by the first mold half-section;

cutting and sealing the superposed sheets around the periphery of the cavity of the first mold half-section, whereby a sheath is formed; and discontinuing the imposition of the pressure differential on the sheets of thermoplastic elastomeric material, to yield a condom comprising the sheath formed by the cut and sealed sheets of thermoplastic elastomeric material.

In another aspect, the present invention relates to an apparatus for stress-softening a tubular article formed of a thermoplastic elastomeric material, and having a closed first end and an open second end, comprising:

a mandril assembly, comprising an elongate, generally cylindrically shaped mandril having a central longitudinal axis and smooth-surfaced distal end portion;

means for selectively longitudinally translating the mandril between a first installation position for installing the tubular article thereon, and a second expansion position;

an elongate confining means having a central longitudinal axis and defining an interior space therewith, positioned coaxially with respect to the mandril;

means for (1) selectively longitudinally translating the confining means between a first retracted position in longitudinally displaced relationship to the distal end portion of the mandril, and a second engaged position at which the confining means engages the mandril assembly so that the mandril is disposed in the interior space of the confining means, and (2) actuating the mandril translating means so that the mandril is thereupon translated to its second expansion position; and means for (1) imposing a pressure differential on a tubular article disposed on the mandril during the longitudinal translation of the mandril from the first installation position to the second expansion position, such that the mandril-mounted tubular article is longitudinally and radially expanded within the confining means, and (2) terminating the pressure differential to relax the expanded tubular article to an unexpanded state and yield same as a stress-softened tubular article.

In a further aspect, the present invention relates to an apparatus for stress-softening a tubular article formed of a thermoplastic elastomeric material, comprising:

an elongate mandril having a central longitudinal axis and a star-shaped cross-section in a plane transverse to the centerl longitudinal axis; and means for imposing a pressure differential on a tubular article positioned over said mandril to force the tubular article into conformity with exterior surfaces of the mandril.

The above-described star-shaped mandril may thus comprise a central longitudinal portion or core, from which a plurality of outwardly extending arms or spokes radially extend.

Other objects and advantages of the invention will be more fully apparent from the ensuing disclosure and appended claims.

BRIEF DESCRIPTION OF THE DRAWINGS

FIG. 23 is a front elevation view of the mandril and housing assembly of the FIG. 20 apparatus, with the housing in a first retracted position.

FIG. 24 is a front elevation view of the mandril and housing assembly of FIG. 23, after the housing has been longitudinally translated to an engaged position, and the tubular article has been expanded by flow of gas through the mandril into the interior volume of the tubular article.

FIG. 25 is a front elevation view of the FIG. 24 mandril and housing assembly, after the pressure into the interior volume of the expanded tubular article has been released, and the tubular article has deflated onto the mandril, and the housing has been retracted to its initial position corresponding to that shown in FIG. 23.

DETAILED DESCRIPTION OF THE INVENTION, AND PREFERRED EMBODIMENTS THEREOF

Figure 1:
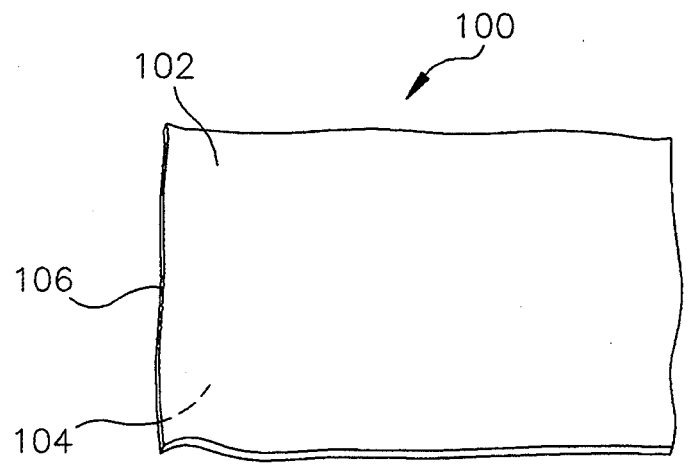
FIG. 1 is a top plan view of a stress-softened thermoplastic elastomeric film according to one embodiment of the present invention.

The present invention is based on the surprising and unexpected discovery that a highly superior stress-softened thermoplastic elastomeric film, characterized by good elongation and elasticity characteristics, reduced elastic modulus, and improved softness, textural, and "hand" characteristics, is achievable by tensionally stretching the film, such that the resulting thermoplastic elastomeric film has at least one of the following characteristics:

(i) a shear stiffness value not exceeding 2.5 gf/cm degree;

(ii) a tensile energy value of at least 1.0 gf/cm/cm$^2$;

(iii) an extensibility at 50 gf/cm load of at least 4.0%;

(iv) a dry heat loss value of at least 16.5 watts/m$^2$/° C.;

(v) a wet heat loss value of at least 22.0 watts/m$^2$/° C.; and (vi) a $Q_{max}$ value not exceeding 12.25 watts/m$^2$/° C.

Preferably the tensional stretching of the film comprises strain which is at least uniaxial in orientation, preferably at least biaxial (e.g., longitudinal and radial), and preferably such tensional stretching is carried out in such manner that the film upon release of the tensional stretching strain is reduced in thickness by at least 10% from its original thickness, to a reduced film thickness which preferably is less than 100 micrometers. The resulting film preferably has at least one of the following characteristics: (i) an elastic modulus at 20% elongation which is at least 15% lower than the elastic modulus at 20% elongation of a corresponding film of the aforementioned original thickness which has not been subjected to the tensional stretching, such original (non-stretched) film sometimes hereinafter being referred to as "native film", and (ii) a break ratio defined by the equation:

$$\frac{(\% \text{ elongation at break})_{stress\text{-}softened\ film}}{(\% \text{ elongation at break})_{native\ film}},$$

which is less than 0.9 in value.

In a preferred embodiment, the stress softened film of the invention has at least one of the following characteristics:

(i) a shear stiffness value of from 0.5 to 2.5 gf/cm degree;
(ii) a tensile energy value of from 1 to 3 gf/cm/cm$^2$;
(iii) an extensibility at 50 gf/cm load of from 4 to 12%;
(iv) a dry heat loss value of from 16.5 to 20.0 watts/m$^2$/° C.;
(v) a wet heat loss value of from 22 to 25 watts/m$^2$/° C.; and
(vi) a $Q_{max}$ value of from 10 to 12.25 watts/m$^2$/° C.

The aforementioned shear stiffness, tensile energy, extensibility, dry heat loss, wet heat loss, and $Q_{max}$ values as used herein are determined by the test procedures described below.

Shear Stiffness Values

The shear stiffness value of the thermoplastic elastomeric film is determined by applying opposing parallel forces to the film by a KES-FB1 tensile-shear tester, of the type described at pages 34–36 of *The Standardization and Analysis of Hand Evaluation,* Second Edition, 1980, by S. Kawabata. These opposing parallel forces are applied until a maximum offset angle of 8° is reached. A tension load of 5 grams force per centimeter (gf/cm) is applied to the specimen for such shear testing, yielding a shear stiffness value as a measure of the conformability of the film material. Numerically, the lower the shear stiffness, sometimes denoted hereinafter as G, the more conformable the film material. The shear stiffness value has units of gf/cm degree.

Tensile Energy Value

The tensile energy value of the thermoplastic elastomeric film is performed on the KES-FB1 tensile-shear tester, by the procedure described at pages 28–30 of the Kawabata text identified above. The tensile energy value measures the stress/strain character of the material at a maximum load of 50 gf/cm. Due to the excessive "stretchiness" of the thermoplastic elastomeric film material, a sample length of 2.5 centimeters is used in such tensile test. The units of the tensile energy value are gf/cm/cm$^2$. The tensile energy is the area under stress/strain curve, and it relates to the energy which is absorbed by the polymer under a specified stress (50 gf/cm). Generally, the more energy the polymer can absorb, the more extensible it is. Thus, higher tensile energy values are associated with higher extensibility of the thermoplastic elastomeric film.

Extensibility at 50 gf/cm Load

The extensibility is measured as percent strain at a maximum load of 50 gf/cm, by the procedure set out at pages 28–30 of the Kawabata text identified above. The units of extensibility are percentages, and extensibility roughly translates to "stretchiness" of the thermoplastic elastomeric film material.

Dry Heat Loss Value

The dry heat loss value, as well as the wet heat loss value, and the $Q_{max}$ value, are measured by a "thermo labo" system for measurement of transient heat transfer and qualities of films and fabrics for assessment of surface warm/cool sensations and energy dissipation. The thermolabo system consists of three components, including: (1) an insulated hot plate fitted into a box with preset temperature control means, to simulate human skin surfaces including body temperature;

(2) a water-box with constant temperature water flow to provide a constant temperature base required for the procedure; and (3) a box containing a thin copper heat capacitor fitted with a temperature sensing device, to measure the amount of heat and the rate of heat flow through film or fabric specimens during testing. The system provides the rate at which heat is extracted from a finite thermal capacity object, such as human skin, through a film or fabric, to be detected. The thermolabo system including the insulative hot plate, water-box, and box containing the heat capacitor fitted with a temperature sensing device, is positioned in an environmental chamber where heat, humidity, and air flow are controlled automatically.

The heat loss values are determined as the heat dissipated from the hot plate through the selected film specimen to air, and is a measure of the thermal insulation properties of the material. For this measurment, the hot plate is placed in a wind tunnel through which is blown air of known temperature and humidity at a standard air velocity of 20 centimeters per second. In this manner, a controlled environment is maintained around the specimen.

In the dry heat loss value determination method, a specimen is placed on the hot plate and the rate of heat loss of the hot plate is measured, in units of watts/m$^2$/° C. The dry heat loss value indicates the ease of heat transfer through the film material to the environment. The greater the heat transfer (heat loss), the more "human-like" the contact with the film will seem. Dry heat loss values are determined without sweat exudation, as conducted in the wet heat loss value determination method, described below.

Wet Meat Loss Value

The wet heat loss value is determined using a sweating hot plate containing four moisture sources with a peristaltic pump used to control water flow. A highly wettable dimensionally stable polyester rayon nonwoven membrane is placed on the hot moist plate and the film specimen is positioned on top thereof. The rate of heat loss of the hot plate is measured. The wet membrane is provided to simulate human skin. It should be noted that the measurement of heat dissipation includes the latent vaporization of water. The rate of water dissipation through the specimen can be obtained approximately as the difference between the dry heat loss value and the wet heat loss value, divided by a, where a is the latent heat of vaporization of the water. The wet heat loss value indicates the ease of heat transfer through the film material to the environment. The greater the heat transfer, the more "human-like" the contact will seem. The thermolabo system is more fully described as to its structure and arrangement in Kawabata, S., et al, "Applications of the New Thermal Tester 'Thermolabo' to the Evaluation of Clothing Comfort, in Objective Measurements: Applications to Product Design and Process Control", Eds., S. Kawabata, et al, The Textile Machinery Society of Japan, 1985.

$Q_{max}$ Value

The thermal transmission properties of material related directly to their "cool" or "warm" feel. The $Q_{max}$ value is a transient response of an (almost) instaneous heat flow into a sample, analogous to what the nerves in the skin perceive in contact with a specific material. Higher values of $Q_{max}$ relate to a cooler feel. For applications such as condoms, tubular bandages, and other film articles in contact with skin surfaces, a lower value of $Q_{max}$ would be preferable. $Q_{max}$ is measured in units of watts/m$^2$/° C., and is defined as the peak value of the rate of flow of heat from the heat capacitor to the surface of a film specimen measured from the moment the capacitor of the thermolabo comes into contact with the surface to be tested. The resulting transient response is similar to that occuring as heat is transferred from the surface of the human skin to the heat sensitive nerves just beneath the skin. $Q_{max}$ thus is indicative of the warmth or coolness of a film surface, and, as mentioned, larger values of $Q_{max}$ indicate cooler feeling films.

In summary, the shear stiffness measures conformability of the material, and the lower the shear stiffness value, the more conformable the material; the tensile energy value is the area under a stress/strain curve, and relates to the energy absorbed by the polymer under specified stress, with higher values indicative of greater extensibility of the film, extensibility being approximately indicative of "stretchiness" of the film; dry heat loss value and wet heat loss value indicate the ease of heat transfer through the material of the film to environment, with higher values indicating a more "human-like" contact; and $Q_{max}$ indicates the transient response to instaneous heat flow into a sample, simulative of what nerves in the skin perceive, with higher values of $Q_{max}$ relating to a cooler feel, and lower values of $Q_{max}$ relating to a warmer feel.

For thermoplastic elastomeric film applications such as condoms and other articles where the film is in contact with the skin, it is generally desirable to have a lowest possible shear stiffness, a highest possible tensile energy, a highest possible extensibility, a highest possible dry as well as wet heat loss value, and a lowest possible $Q_{max}$ value. It has suprisingly been found that stress-softening of thermoplastic elastomeric films provides such optimal relative magnitudes of these shear stiffness, tensile energy, extensibility, dry heat loss, wet heat loss, and $Q_{max}$ values, relative to corresponding films which have not been stress-softened, as will be shown more fully hereinafter by empirical data in the Examples.

In the stress-softened thermoplastic elastomeric films and film articles of the invention, the film advantageously is formed of a polymer comprising (i) hydrocarbonaceous chain moieties constituting relatively softer segments of the polymer, and (ii) relatively harder segments. The terms "softer" and "harder" are of course relative to one another; in an absolute aspect, the softer segments must be sufficiently soft to impart elastomeric character to the film, while the harder segments impart thermoplastic character to the film material. Preferably, the softer segments are hydrocarbonaceous chain moieties which are derived from polymerizable monomers or precursors, such as olefins, e.g., ethylene, propylene, etc., as well as dienes, including butadiene, isoprene, etc. The hard segments may be formed of styrenic or other arylene vinyl monomers, or such hard segments alternatively may comprise urethane linkages, or other hard moieties, chains, linkages, and the like, which impart the requisite thermoplasticity and physical properties to the thermoplastic elastomeric material, and render it suitable for its intended purpose.

In the stress-softening process which is applied to films and film articles of the present invention, stretching of the film is carried out, which is at least uniaxial in character, and more preferably at least biaxial. During this stretching, many of the elastic soft segments of the thermoplastic elastomer are pulled taut, and exert stress on the hard segments which have aggregated in the material. The hard segments during such stretching are torn apart to create smaller, more widely-dispersed hard segments. It is speculated that these hard segments slip into the new positions in the microstructure of the material, the stresses on the soft segments in the native (previously unstretched) material are relieved, and the soft segments assume a preferred coiled configuration.

The overall result of such stretching is that most of the soft segments become coiled, with fewer being stretched between hard segments, as is the case in the unstretched native material. The new microstructural configuration of hard segments and soft segments may be manifested in a significantly reduced elastic modulus of the film material. There is no reorientation of crystallites and no increase in crystallinity, such as occurs when crystalline or semi-crystalline polymers are subjected to stress conditions resulting in stretching or distension of the crystalline or semi-crystalline polymer film. There is also no chemical reaction to microstructurally fix the hard segments in position, or to complete the polymerization process, or to effect cross-linking, as is the case in chemically-modified elastic polymer films. Thus, the stress-softening of the present invention is a substantially different and non-analogous process to the stress-modification of crystalline or semi-crystalline polymer films, and to the chemical reactions employed to produce chemically modified polymer films. The stress-softening of the present invention suitably and preferably is carried out at ambient, e.g., room temperature conditions, as for example a temperature in the range of about 5° C. to about 40° C.

The novelty of the present invention is evident when contrasted with techniques conventionally utilized by resin producers to modify resins to improve the softness of films produced therefrom. The conventional method of improving the softness of films of materials such as polyester-based polyurethanes or polyether-based polyurethanes has been to alter the chain links of the soft polyester or polyether segments, and to reduce the concentration of hard segments. A resulting deficiency, however, is that polyurethane materials softened by such approach are lacking in dimensional stability. The stress-softening methodology of the present invention, however, does not require such compositional alteration of the thermoplastic elastomeric film material, and achieves films of superior softness and suitable stability from conventional and readily available thermoplastic elastomeric film materials.

Illustrative of thermoplastic elastomeric materials which may find utility in the broad practice of the present invention are: polyurethane materials, as for example the polyester-based polyurethane materials commercially available from Mobay Corporation (Plastics and Rubber Division, Pittsburgh, Pa.) under the trademark Texin ®, the thermoplastic polyurethane elastomers which are commercially available from BASF Corporation (Parsippany, N.J.) under the trademark Elastollan ®, and the thermoplastic polyurethane elastomers available under the trademark Platilon ® from Atochem, Inc. (Glen Rock, N.J.); polyether elastomers, such as the block copolymers of polybutylene terephthalate and long-chain polyether glycols, which are available commercially from E. I. DuPont de Nemours and Company, Inc. (Polymer Products Department, Engineering Polymers Division, Wilmington, Del.)

under the trademark HYTREL®; polyether block amides, such as those commercially available from Atochem, Inc. (Glen Rock, N.J.) under the trademark Pebax®; multiblock rubber-based copolymers, particularly those in which the rubber block component is based on butadiene, isoprene, or ethylene/butylene, such as the multiblock rubber-based copolymers commercially available from Shell Chemical Company (Houston, Tex.) under the trademark Kraton®; as well as any other suitable homopolymers and copolymers, and mixtures, alloys, and composites thereof.

Among the foregoing materials, polyether- and polyester-based polyurethanes, and multiblock rubber-based copolymers are particularly preferred.

The most preferred thermoplastic materials for forming stress-softened films and film articles in accordance with the present invention are the aforementioned thermoplastic polyurethane elastomers commercially available under the trademarks Elastollan® and Platilon®.

When multiblock rubber-based copolymers are employed as materials of construction for the articles of the present invention, their composition may be varied widely. The non-rubber repeating units of the copolymer may be derived from any suitable monomer(s), as for example, (meth)acrylate esters, such as methyl methacrylate, cyclohexylmethacrylate, etc.; vinyl arylenes, such as styrene; etc.

In general, the non-rubber blocks in the multiblock rubber-based copolymer preferably are derived from monomer(s) which are non-elastomeric in character, so that "soft" rubber blocks and "hard" non-elastomeric blocks are provided in the multiblock copolymer. Such hard blocks may suitably be derived from monomers having a glass transition temperature ($T_g$) of at least about 50° C., with styrene being generally preferred. The rubber block of such multiblock copolymers may be formed of repeating units derived from synthetic rubbers such as butadiene, isoprene, ethylene/butylene, etc., with butadiene and ethylene/butylene elastomeric blocks generally being preferred.

The most preferred multiblock rubber-based copolymers are those having an A-B-A structure comprising polystyrene endblocks and an elastomeric midblock.

Illustrative multiblock butadiene-based copolymers which may be usefully employed in the broad practice of the present invention include those variously described in U.S. Pat. Nos. 3,297,793; 3,595,942; 3,402,159; 3,842,029; and 3,694,523, the disclosures of which hereby are incorporated by reference herein. Various multiblock butadiene-styrene copolymers may be usefully employed to form the films and film articles of the present invention, such as the aforementioned triblock ethylene-butadiene-styrene copolymers commercially available under the trademark Kraton® from Shell Chemical Company (Houston, Tex.) and small block butadiene-styrene copolymers commercialized by Firestone Synthetic Rubber & Latex Company (Akron, Ohio) under the trademark Stereon®.

In the general use of a multiblock rubber-based copolymer as the material of construction for the films and film articles of the present invention, the copolymer material preferably is characterized by the following physical properties: a Shore A hardness of from about 25 to about 100; a tensile strength of from about 500 to about 4500 psi ; a 300% modulus of from about 120 to about 1,000 psi; and an ultimate elongation of from about 200 to about 1400%.

With reference to the use of polyurethanes as materials of construction for the films and film articles of the present invention, preferred material characteristics include: a specific gravity of from about 1.00 to about 1.25; a Shore A hardness from about 80 to about 100; a break tensile stress from about 4500 to about 6,000 psi; a tensile stress at 50% elongation of from about 400 to about 2400 psi; an ultimate elongation of from about 350% to about 600%; a flexural modulus of from about 4,000 to about 37,000 psi; and a tear strength of from about 500 to about 1,000 pli.

The stress-softened thermoplastic elastomer films of the present invention may be employed to form any of a wide variety of articles, including, for example, mattress and pillow covers, rain gear and other garment articles, shopping bags, vehicular covers, umbrellas, canopies, prophylactics, finger cots, tubular bandages, etc. In addition, the invention comprehends the formation or fabrication of film articles comprising unstressed native thermoplastic elastomeric films, which then are stress-softened to provide the resulting stress-softened film as a component part of such articles. Examples include the stress-softened thermoplastic elastomeric condoms described hereinafter, which may be stress-softened contemporaneously with their fabrication, either during the fabrication or formation process, or subsequent thereto.

Referring now to the drawings, FIG. 1 shows a top plan view of a stress-softened thermoplastic elastomeric film 100, reposed in a lay-flat conformation. The film 100 is of generally planar form, having a main top surface 102 and a main bottom surface 104 defining a thickness therebetween, as shown by edge 106.

The film 100 has a thickness of less than 100 micrometers. This thickness of film 100 is a reduced thickness as a result of stress-softening, and is at least 10% lower than the thickness of the native, non-stress-softened film which was used to produce film 100 by stress-softening. As an example, the initial native film thickness (prior to stress-softening) may be 25 micrometers, which may be reduced by the stress-softening treatment to a thickness of 20 micrometers. As another example, a thermoplastic elastomeric film of 40 micrometers initial thickness may be reduced by stress-softening treatment to a thickness of 30 micrometers.

More specifically, the stress-softened film of the present invention is suitably constituted by a film which has been reduced in thickness by tensional stretching of the film. The tensional stretching may be uniaxial in character, or biaxial or otherwise polyaxial. The tensional stretching of the film comprises strain or displacement (extension) of the film which suitably enhances at least one of the shear stiffness, tensile energy, extensibility, dry heat loss, wet heat loss, and $Q_{max}$ values of the film.

The stress-softened film 100 preferably has at least one of the following characteristics: (i) an elastic modulus at 20% elongation which is at least 15% lower than the elastic modulus at 20% elongation of a corresponding native, non-stress-softened film of thickness corresponding to the original thickness of the stress-softened film, and (ii) a break ratio value defined by the equation $$\frac{(\% \text{ elongation at break})_{stress\text{-}softened\,film}}{(\% \text{ elongation at break})_{native\,film}},$$

which is less than 0.9 in value.

Figure 2:
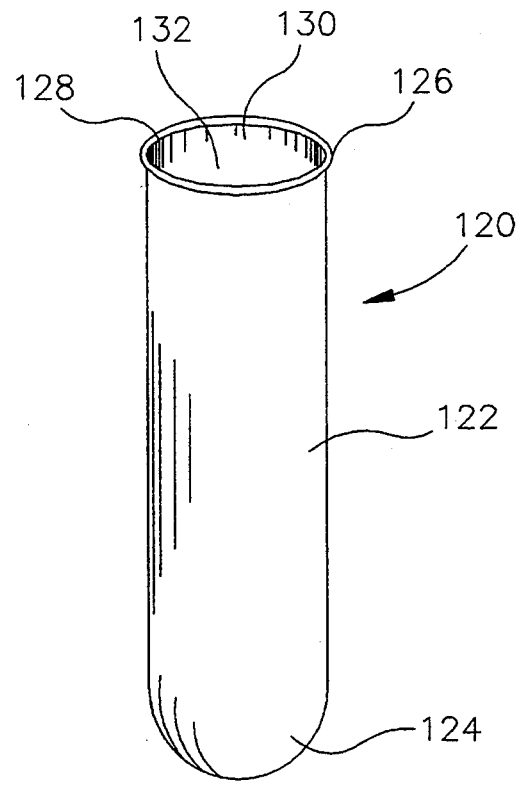
FIG. 2 is a perspective view of a condom including a sheath formed of stress-softened thermoplastic elastomeric film material, according to another embodiment of the invention.

FIG. 2 is a perspective view, in elevation, of a condom article according to one embodiment of the present invention. The condom 120 comprises a generally tubular sheath 122 which is closed at a distal end 124 thereof, and open at a proximal end 126 thereof. As shown, the proximal extremity of the tubular sheath is circumscribed by a bead, filament, or other border element 128 circumscribing the proximal opening 130 of the sheath. The sheath thereby encloses and defines an interior volume 132 of the condom accommodating the insertion of a penis thereinto for use. The tubular sheath of the condom shown in FIG. 2 suitably comprises a stress-softened thermoplastic elastomeric film in accordance with the present invention, as for example a stress-softened polyester-based polyurethane material.

The condom shown in FIG. 2 may be formed of a film which is already stress-softened in character, or alternatively, the condom may initially be formed as generally shown in FIG. 2, followed by stress-softening of the sheath material by longitudinal and radial expansion of the condom, as hereinafter more fully described. The condom may be formed in any suitable manner, including blow forming the tubular main sheath portion of the condom from a suitable thermoplastic elastomeric material, as more fully described in U.S. Pat. No. 4,964,416, the disclosure of which hereby is incorporated herein by reference.

The condom may also be formed by heat-sealing or otherwise joining sheets of thermoplastic elastomeric material to one another to define the main sheath portion of the condom. For example, the condom may be formed by superposing corresponding sheets of a thermoplastic elastomeric material, and heat-sealing and severing same to form the condom article comprising a tubular main sheath portion having a closed distal end and a proximal open end. Preferably, the condom so formed will have perimetral edges which are heat-sealed in the desired configuration, e.g., with a surface profile defining an elongated U-shape.

The condom articles of the present invention may be of generally cylindrical shape. Alternatively, it may be suitable in some instances to utilize the condom of the present invention in the form of a baggy-type penile enclosure which is wrapped about the penis for use, and which is retained in relatively looser configuration on the penis than are the condom articles of generally cylindrical shape which closely overfit the penis, and which are rolled or pulled onto the penis for use.

Thus, the specific structure of condom articles of the present invention may be widely varied, depending on the particular mode of application intended, and the specific thermoplastic elastomeric materials of construction which are employed.

Figure 3:
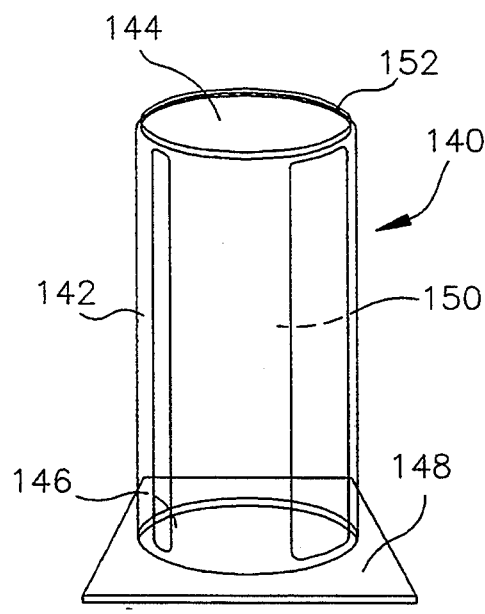
FIG. 3 is a perspective view of an expansion chamber, within which a stress-softened tubular article may be formed in accordance with one embodiment of the present invention.
Figure 4:
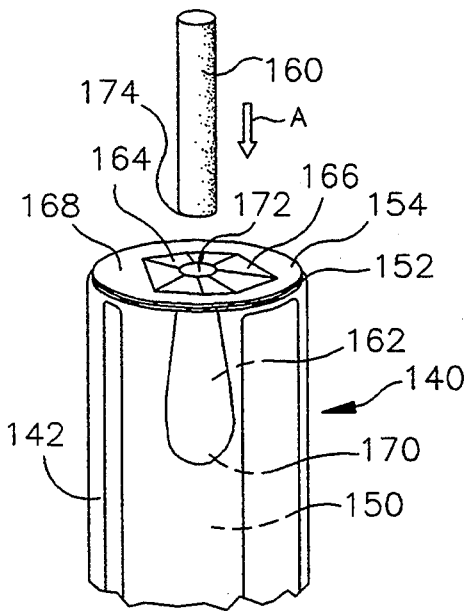
FIG. 4 is a partial perspective view of the expansion chamber of FIG. 3, as associated with a mounted tubular film article and a mandril.
Figure 5:
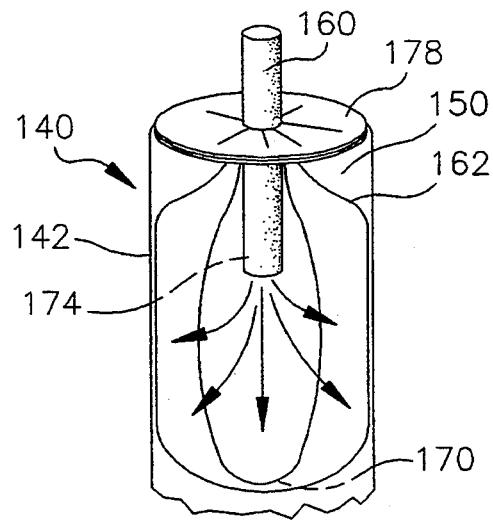
FIG. 5 is a perspective view of the expansion chamber of FIGS. 3 and 4, with the mandril inserted partially thereinto and with the tubular article being radially and longitudinally expanded by fluid pressure, for stress-softening of the film material forming the article.

FIGS. 3–5 illustrate apparatus and methodology for forming a stress-softened thermoplastic elastomeric condom according to one embodiment of the present invention.

FIG. 3 is a perspective view in elevation of an expansion chamber 140, comprising a cylindrical housing 142 having an open upper end 144 and a lower end 146 which is joined to and closed at the lower end by the base member 148. The cylindrical housing may for example be adhesively bonded or otherwise leak-tightly affixed along its bottom edge surface to the base member 148, to provide an interior volume 150 in the cylindrical housing. The cylindrical housing and base member may be formed of any suitable materials of construction, as for example glass, metal, or plastic. The housing may, for example, be formed of a clear acrylic plastic, facilitating viewing of the tubular article being formed in the interior volume 150, as hereinafter more fully described.

The upper end 152 of the cylindrical housing 142 is suitably formed for mating with a cylindrical element 154 as shown in FIG. 4, which is a perspective elevation view of a portion of the expansion chamber 140, shown with the associated mandril 160.

The disk element 154 is provided with a central opening (not visible in FIG. 4) through which tubular article 162 is inserted, to downwardly hang from the disk element with the flanges 164 and 166 of the tubular article 162 reposing on the main top surface 168 of disk element 154.

By this arrangement, the tubular article 162, having a closed distal end 170 and an open proximal end 172, is downwardly suspended in the interior volume 150 of the cylindrical housing 142.

The mandril 160 is shaped to pass through proximal opening 172 of the tubular article 162 and to downwardly stretch the tubular article as the mandril is downwardly translated with the tip 174 of the mandril being in contact with the closed distal end 172 of the tubular article. The tubular article thereby is stretched with the mandril to assure uniform axial stretching and thickness. Thus, the mandril 160 is inserted downwardly into the interior space of the tubular article 162, by translation in the direction shown in FIG. 4 by arrow A. The mandril has an open lower end at its tip 174, and once reposed in the elongated tubular article 162 is supplied with pressurized fluid from a suitable source (not shown), which flows through the hollow, open-ended mandril and into the interior of the tubular article 162, as shown in FIG. 5.

For the purpose of maintaining a suitable pressure differential across the thermoplastic elastomeric film of the tubular article 162, the expansion chamber 140 may be provided with a screw-type top 178, or other appropriate closure means for maintaining the disk element 154 in position and secured against movement caused by expansion of the tubular article during the introduction of pressurized gas or other fluid into the tubular article.

As a result of the introduction of pressurized fluid, the tubular article 162, which is formed of a thermoplastic elastomeric film material, is radially expanded so that the exterior surface of the sheath comes into engagement with the bounding wall of the cylindrical housing 142, while concurrently, the tubular article is longitudinally expanded, so that its distal end 170 is downwardly displaced from the tip 174 of the mandril 160. The distal portion of the expanded tubular article may be unconfined within the interior volume 150 of the cylindrical housing 142, or alternatively, the tubular article may be expanded until the distal portion 170 thereof is in abutting contact with the base member 148 defining the floor of the interior volume 150.

In any event, the thermoplastic elastomeric tubular article 162 is biaxially stretched (radially, and longitudinally) to stress-soften the tubular article. When the desired extent of expansion and pressurization has been achieved, the flow of gas into the mandril 160 may be discontinued to deflate the tubular article onto the mandril, following which the mandril and tubular article can be withdrawn from the expansion chamber. In this respect, it may be desirable in some instances to apply a vacuum to the hollow mandril, whereby the stress-softened tubular article is suctioned onto the exterior surface of the mandril, to facilitate removal of the tubular article from the expansion chamber 140.

Alternatively, rather than pressurizing the interior of the tubular article by flow of pressurized gas through the hollow mandril, it may be desirable in some instances to draw an exterior vacuum on the tubular article, by evacuation of the interior volume 150 of the expansion chamber 140, or to combine interior pressurization of the tubular article with the imposition of vacuum on its exterior surface, to facilitate the desired stretching and stress-softening of the article.

Figure 6:
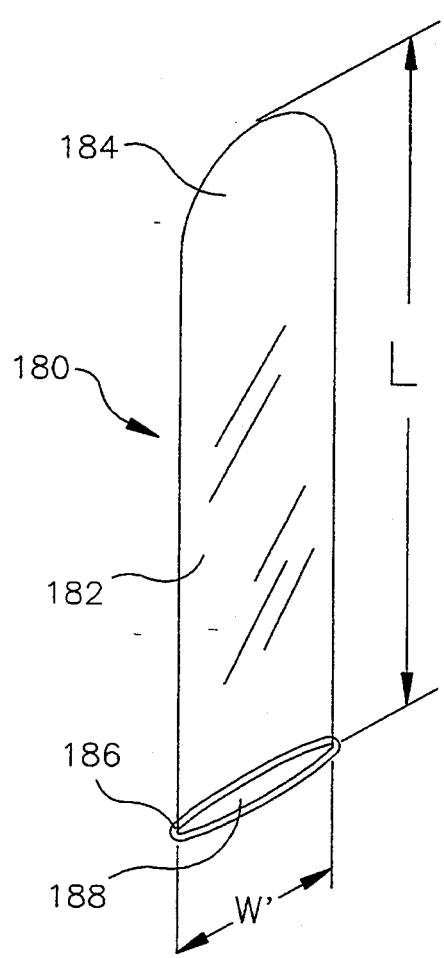
FIG. 6 is a perspective view of a starting tubular film article, such as may be employed in connection with the stress-softening apparatus shown in FIGS. 3–5.

FIG. 6 shows a perspective elevation view of a non-stress-softened thermoplastic elastomeric film article 180 of tubular shape, prior to stress-softening treatment thereof. The corresponding expanded and stress-softened tubular article 180 is shown in FIG. 7, in perspective elevation view.

Referring first to FIG. 6, the tubular article 180 comprises a generally tubular-shaped main sheath portion 182 having a closed distal end 184 and an open proximal end 186 featuring opening 188. The sheath is formed of a non-stress-softened thermoplastic elastomeric film, for example having a thickness in the range of from about 25 to about 40 micrometers. The length L of the tubular article may be on the order of 7 inches, and the width W (lay-flat diameter) thereof may be on the order of 2 inches. The tubular article 180 shown in FIG. 6 may be biaxially stretched by stress-softening treatment as described in connection with FIGS. 3-5 as disclosed above. The resulting tubular article 180 may suitably have the form shown in FIG. 7, wherein the sheath 182 of the article is stress-softened in character, with a thickness which may on the order of 25-35 micrometers, and about 35% thinner than the sheath wall thickness of the unstretched tubular article shown in FIG. 6.

Figure 7:
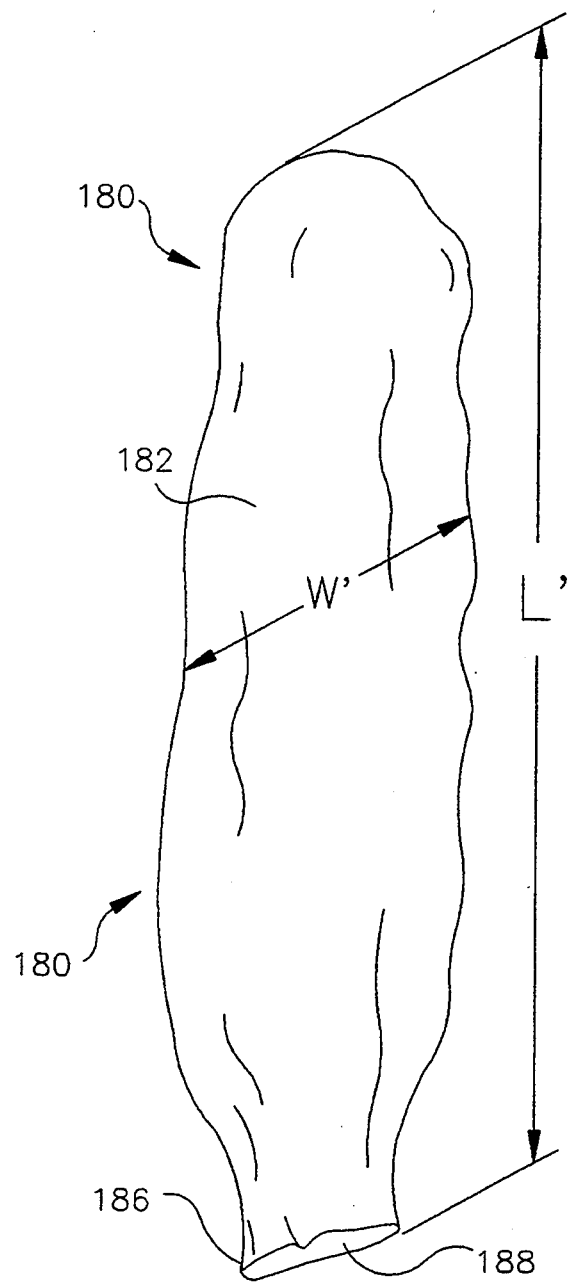
FIG. 7 is a perspective view of a tubular film article corresponding to the starting film article of FIG. 6, which has been stress-softened by processing in the apparatus shown in FIGS. 3–5.

As a result of the biaxial stretching of the tubular article shown in FIG. 6, the stress-softened article shown in FIG. 7 may have an expanded length L' which is on the order of 8.5 inches, and an expanded width W' (lay-flat diameter) which is on the order of 2-3 inches. Thus, the resulting tubular article of FIG. 7 could be approximately 50% larger in total surface area (exterior surface area of the sheath), as compared to the unexpanded article of FIG. 6.

The tubular article of FIGS. 6 and 7 may advantageously be employed as a condom. As a result of the original positioning of the non-stress-softened tubular article as secured by the disk element 154 and screw-type top 178 associated with the expansion chamber (see FIG. 5), it is seen that the proximal end 186 of the stress-softened article shown in FIG. 7 remains unexpanded. This proximal end forms a "neck" of the stress-softened article which is of generally smaller diameter (lateral dimension), as compared to the main expanded portion of the sheath 182. In this manner, the unexpanded neck portion of the article may be advantageously utilized, when the article is employed as a condom, to retain the tubular article on the penis of a wearer, and also to prevent exchange of coital fluids between coital partners.

It will be seen that the article of FIG. 7 after stress-softening treatment is of a larger, baggier configuration, as opposed to the starting article shown in FIG. 6, albeit still of a generally tubular shape. In some instances, however, it may be desired to retain a more closely cylindrical, tubular configuration than is afforded by the stress-softening expansion of the entire sheath as shown and described with reference to FIGS. 3-7.

Figure 8:
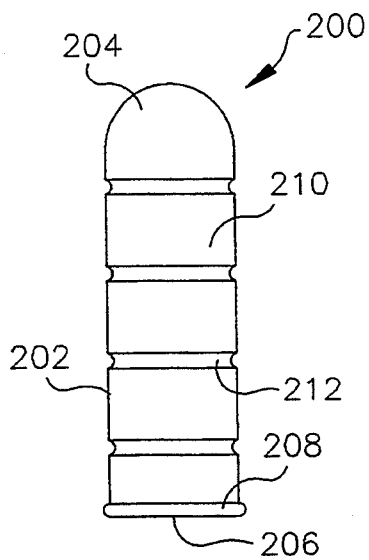
FIG. 8 is a side elevation view of a condom according to another embodiment of the present invention, featuring a series of longitudinally spaced-apart stress-softened sections, alternating with non-stress-softened band regions of the sheath.

FIG. 8 is an elevation view of a condom formed of a thermoplastic elastomeric film material, which retains a cylindrical, tubular appearance, yet is stress-softened over the majority of its film surface area.

The tubular article 200 shown in FIG. 8 comprises a main sheath portion 202 of generally cylindrical shape, with a closed distal end 204 and an open proximal end 206 bounded by a bead or filament 208.

The sheath of this condom features a series of longitudinally spaced-apart stress-softened portions 210 which alternate with and are separated from one another by non-stress-softened bands 212.

In the structure shown in FIG. 8, the tubular article 200 features a number of bands 212 which are less elastic, and less soft than the stress-softened portions 210, yet the surface area of the sheath 202 which is stress-softened in character is on the order of 90%–95% of the overall film area of the sheath.

Furthermore, in usage as a condom, the bands 212 of the tubular article shown in FIG. 8 compressively engage the penis along its length, to provide an enhanced retention ability of the condom on the penis. This enhances retention ability and minimizes the possibility that the condom may be disengaged from the penis during coital activity or detumescence, and also improves the ability of the condom to retain ejaculate therein. The provision of the non-stress-softened bands 212 thereby enhances the function of the condom as a contraceptive barrier means, and as a means of reducing the incidence of sexually transmitted disease.

Figure 9A:
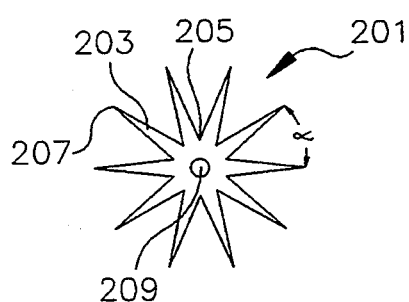
FIG. 9A is a top plan view of a star-shaped mandril, such as may be usefully employed to produce a stress-softened tubular article.
Figure 9B:
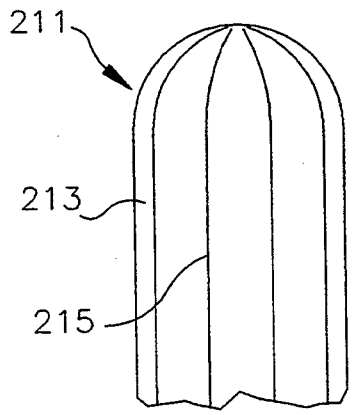
FIG. 9B is a perspective view of the distal portion of a tubular article produced by the use of a mandril of the type shown in FIG. 9A.
Figure 9:
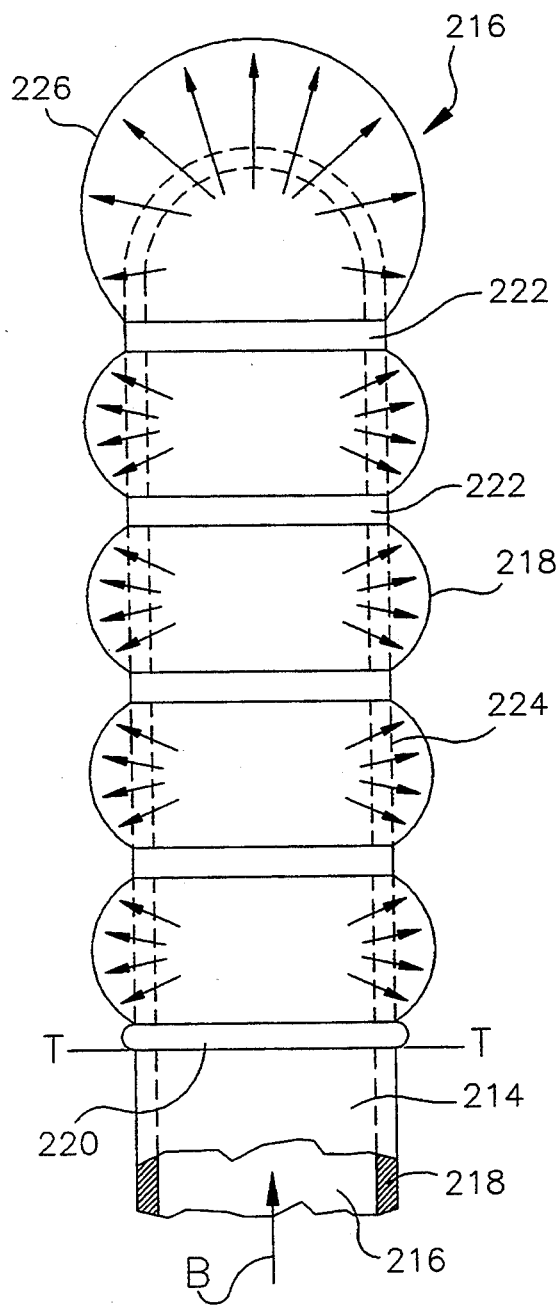
FIG. 9 is an elevation view of a condom of the type shown in FIG. 8 being formed on a porous mandril through which gas is flowed under pressure to distend the sheath in the sections to be stress-softened.

FIG. 9 is an elevation view, in partial section, of a mandril 214, on which a tubular article 216 is being stress-softened to forth a condom of the type shown and described with reference to FIG. 8.

The tubular article 216 shown in FIG. 9 comprises a sheath 218 formed of thermoplastic elastomeric material, which has been pulled or unrolled onto the exterior surface of mandril 214.

The mandril 214 is of hollow configuration, enclosing an interior space 216 into which pressurized gas or other elevated pressure fluid may be introduced from a suitable source (not shown) joined in closed flow communication therewith. Gas flow is introduced into the hollow mandril 214 in the direction of the arrow B. The wall 218 of the mandril above the baseline T-T is porous in character, so that the pressurized gas introduced into the interior space 216 of the mandril can pass through the porous mandril wall. The tubular article is mounted on the mandril, such that the bead or filament 220 circumscribing the proximal open end of the tubular article is positioned at or slightly below baseline T-T. Prior to introduction of gas flow into the interior space 216 of the mandril, a series of retaining bands 222 are positioned on the exterior surface of the tubular article in longitudinally spaced-apart relation to one another, to secure the sheath areas of the article covered thereby so that such areas are in contact with the mandril during the subsequent introduction of the pressurized gas into the interior space 216 of the mandril and outward flow of such pressurized gas through the porous wall of the mandril.

The band members 222 may be any suitable elastic bands which tightly compressively bear against the exterior surface of the mandril-mounted tubular article, and prevent distension or expansion of the tubular article surface regions which are covered by such bands. The bands may for example be formed of rubber or other elastic material, of a relatively firm and tight character when compressively mounted on the tubular article on the mandril.

Thus, when pressurized fluid is introduced into the hollow interior space 216 of mandril 214, the pressurized fluid flows through the porous wall of the mandril outwardly against the thermoplastic elastomeric film of the sheath, resulting in distension of the portions of the sheath which are not confined by the retaining bands 222. In this fashion, the portions of the sheath 218 between adjacent retaining bands, e.g., unconfined sheath portions 224, 226 are distended, or bulged, outwardly as the pressurized fluid passes through the porous mandril wall and forces the unconfined sheath portions into the pressure-deformed conformations shown in FIG. 9. At the distal portion 226, the pressurization of the interior surface of the thermoplastic elastomeric film results in a bulbous conformation of the film being produced.

The expansion of the sheath of the tubular article may be carried out substantially as shown in FIG. 9, or alternatively, the expansion may be carried out inside of an expansion chamber of the type shown in FIG. 3, which is inverted and placed over the mandril-mounted tubular article during expansion of the sheath, so that the cylindrical wall and base member of the expansion chamber confine the extent of expansion of the tubular article. In any event, subsequent to expansion of the unconfined portions of the tubular article to the desired extent, pressurized fluid flow into the hollow mandril 214 is discontinued, and the mandril is depressurized, following which the expanded portions 224, 226 of the sheath 218 collapse over the mandril in a distended form relative to the original shape of the sheath. Alternatively, the mandril may be only partially depressurized, so that the sheath is maintained in a slightly inflated state to facilitate its removal from the mandril. The retaining bands then may be removed from the tubular article, and the article may be removed from the mandril, resulting in the stress-softened tubular article configuration shown in FIG. 8.

As an alternative to the stress-softening method shown and described with reference to FIG. 9, the retaining bands 222 may be deleted in some instances, if other suitable means of confining the film on the mandril in the band regions is employed, which obviates the use of the retaining bands 222. For example, it may be feasible in some instances to utilize an interior manifold structure in the mandril 214, which selectively applies vacuum to the band regions of the tubular article, to confine the band regions in contact with the mandril exterior surface during the fluid pressurization resulting in distension of the unconfined sheath portions 224, 226.

As a still further alternative, it may be feasible in some instances to utilize a mechanical gripping means securing the film to the mandril at the desired band regions, during fluid pressurization of the unconfined portions of the sheath.

It will be recognized that the use of confined and unconfined regions of a film to pressurizingly distend the unconfined areas and produce a stress-softened film in which unconfined areas are stress-softened and confined areas are non-stress-softened, may be broadly applied, and is not restricted in utility to the specific banded pattern of the sheath shown in FIG. 8. For example, the confined areas of the film, during the pressure distension of unconfined areas, may be vertical rather than horizontal (circumferential) in character, whereby the stress-softened tubular article will comprise a series of longitudinally extending non-stress-softened bands. As a further example, the confined areas may be criss-crossed, serpentine, or any other suitable geometry, as necessary or desired in a given application to produce a film or film article comprising stress-softened and non-stress-softened portions.

Another approach would be to provide a corresponding forming dye whose interior cavity approximates the shape shown by the distended tubular article in FIG. 9, with the non-stress-softened (precursor) tubular article being introduced into the die cavity and thereafter subjected to internal pressurization causing the tubular film to expand into engagement with the interior surfaces of the die. Subsequently, the pressurized tubular article can be depressurized and removed from the die as a stress-softened product article.

FIG. 9A is a top plan view of a star-shaped mandril which may be employed in forming a stress-softened tubular article.

As shown in FIG. 9A, the mandril 201 comprises a central tubular member 209 from which radiate a series of projections 203 which extend outwardly to a radial extremity 207. As shown, the respective projections 203 are in spaced relationship to one another to form a series of intervening spaces 205 in the nature of valleys between the respective projections of the mandril. The mandril is constructed such that the tubular member 209 is hollow and communicates in gas flow communication relationship with the innermost troughs of the intervening spaces 205, so that gas may be withdrawn by suction from such troughs into the tubular member 209 and subsequently withdrawn therefrom, e.g., by suitable vacuum drawing means (not shown for clarity). The view shown in FIG. 9A is a top plan view, it being recognized that the mandril has a significant longitudinal extent. The angle $\alpha$ between the respective projections 203 of the mandril may be on the order of 60°, as shown. Alternatively, a greater or lesser number of projections may be employed, as desirable or otherwise appropriate to the specific tubular film article being processed.

In use of the star-shaped mandril 201 shown in FIG. 9A, a tubular precursor article (i.e., one which is non-stress-softened) is placed over the mandril so that the extremities 207 of the respective projections 203 are in contact with the interior surface of the precursor tubular article. Subsequent to such positioning of the precursor article of the mandril, gas is withdrawn from the interior spaces 205 through suitable gas flow openings (not shown) in the respective troughs of the intervening spaces 205. Alternatively, the interior passage of the mandril may be at atmospheric pressure and a superatmospheric pressure may be exteriorly imposed on the film of the tubular article mounted on the mandril. In any case, a pressure differential is imposed on the film of the tubular article. In this manner, the tubular film material is directed into the intervening spaces 205 between the projections 203, so that the film conforms to the shape of the mandril.

Subsequently, the vacuum drawing through the gas flow openings in the troughs of intervening spaces 205 and hollow tubular member 209 is discontinued, and the resulting tubular article comprising stress-softened film is removed from the mandril. A distal portion of a tubular article processed on the mandril of FIG. 9A, is shown in perspective view in FIG. 9B. As there shown, the tubular article 211 comprises a stress-softened film 213. The film includes longitudinally extending wrinkles 215 reflecting the shape imparted to the film during its stress-softening on the mandril.

Figure 10:
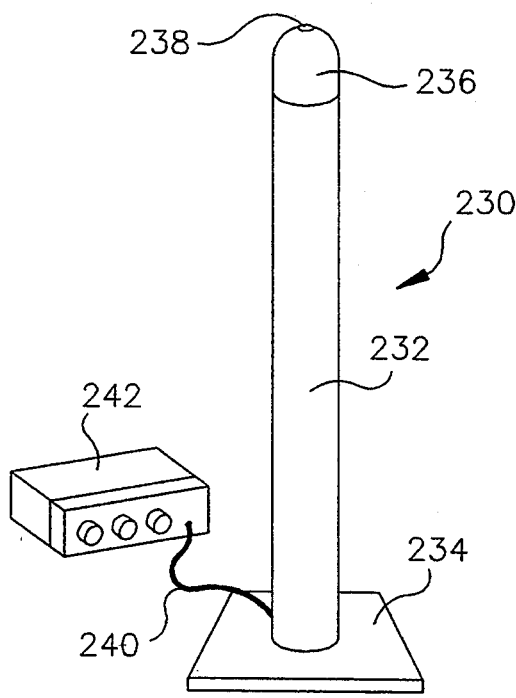
FIG. 10 is a perspective view of a mandril and fluid supply assembly for forming a stress-softened tubular article according to one embodiment of the invention.
Figure 11:
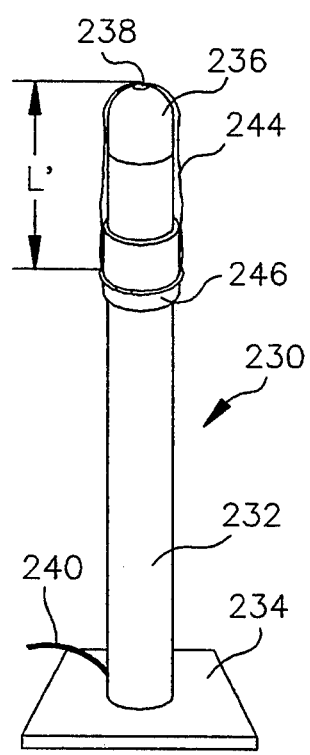
FIG. 11 is a perspective view of a portion of the FIG. 10 assembly, showing a tubular article being mounted on the upper end of the mandril and secured with a proximal collar member.
Figure 12:
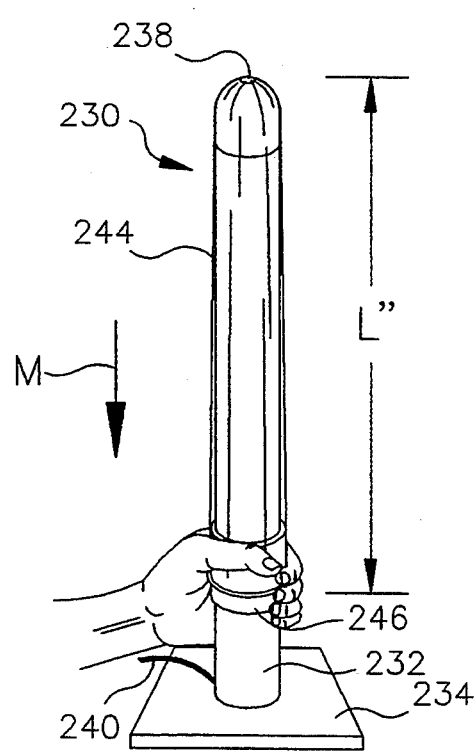
FIG. 12 is a perspective view of a portion of the FIG. 10 assembly, showing the tubular article of FIG. 11 being longitudinally stretched by manual downward movement of the collar member on the mandril.

FIGS. 10–12 are perspective elevation views of a mandril and fluid dispenser assembly for forming stress-softened tubular articles of thermoplastic elastomeric film.

Referring to FIG. 10, the assembly 230 comprises a mandril 232 mounted at its lower end on a planar base member 234. The mandril at its upper end features a smooth rounded-tip member 236, which may be formed of suitable low-friction, smooth material, such as Delrin ® polyacetal (E.I. DuPont de Nemours and Company, Wilmington, Del.). The main shaft of the mandril 232, as well as its tip member 236, may have a diameter on the order of about 1 inch. The mandril 232 is hollow in structure, and has a distal opening 238 in the tip member 236, for flow of fluid therethrough. The hollow mandril 232 at its lower extremity is joined to one end of a fluid flow conduit 240 which is joined at its opposite end to an electronic fluid dispenser unit 242, as shown. The electronic fluid dispenser unit 242 may in turn be joined to any suitable source of fluid (not shown), as for example, air, water, or other gas or liquid which may be flowed under pressure into the hollow mandril 232 from conduit 240, and subsequently issued from the distal opening 238 in distal tip member 236 of the mandril.

FIG. 11 is a perspective elevation view of the mandril assembly 230, of the type shown in FIG. 10, but without the electronic fluid dispenser unit 242 being shown. Mounted on the upper end of mandril 232 and overlying the mandril exterior surface is a tubular article 244 formed of a thermoplastic elastomeric film. This tubular article is secured at its lower extremity to a collar 246, which is slidable in character along the length of mandril 232. As shown in FIG. 11, the tubular article 244 as initially reposed on the upper end portion of mandril 232 (in unstretched condition) has a length L'.

FIG. 12 is a perspective elevation view of the assembly 230 shown in FIG. 11, but wherein the collar 246 has been manually grasped, and downwardly translated in the direction indicated by arrow M, such that the longitudinally extended tubular article 244 has an extended length L".

In this manner, the tubular article is longitudinally stretched. Subsequent to such stretching, with the tubular article being held at length L", fluid under pressure is flowed through conduit 240 from the electronic fluid dispensing unit 242 (not shown in FIG. 12). The fluid then passes through the hollow interior of mandril 232 and through the distal opening 238 into the tubular article mounted on the mandril, to force the tubular article 244 radially outwardly, so that the thermoplastic elastomeric film of the article is biaxially stretched (longitudinally, and radially). If desired, the radial expansion may be limited by positioning an expansion chamber, of the general type shown and described with reference to FIG. 3, over the stretched tubular article shown in FIG. 12, so that during subsequent fluid pressurization, the outwardly distending thermoplastic elastomeric film comes into contact with the interior surfaces of the confining walls of the expansion chamber, to produce a desired symmetrical degree of radial expansion. Alternatively, the expansion chamber may be deleted in favor of free radial distension under the effect of the pressurized fluid pumped through mandril 232 and into the space between the exterior surface of the mandril and the interior surface of the tubular article.

Figure 13:
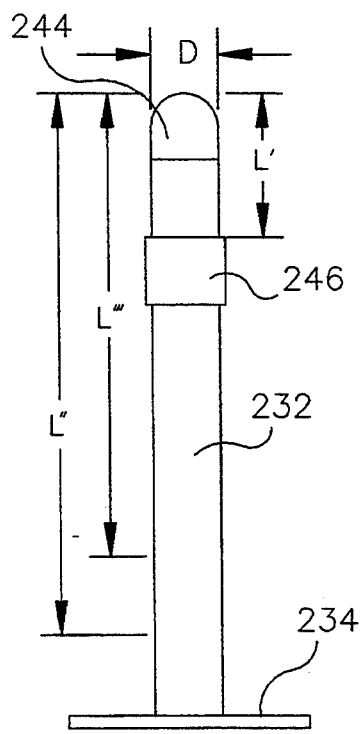
FIG. 13 is a side elevation view, in schematic form, of the mandril apparatus of FIGS. 10–12, showing the dimensional characteristics thereof.

FIG. 13 is a schematic representation of the mandril employed in the assembly shown in FIGS. 10–12.

The mandril 232 is shown in FIG. 13 as mounted on base member 234, and as having collar 246 disposed at an upper portion of the mandril. In such position, corresponding to that shown in FIG. 11, the unstretched length L' of the tubular article 244 may for example be on the order of about 5 inches, as measured from the distal tip of the tubular article to the upper end of the collar 246. The diameter of the mandril, D, may be on the order of about 1.3 inches, and the tubular article may likewise have a diameter approximating such value.

The tubular article during the stretching step shown in FIG. 12 is stretched axially on the mandril to a length L" which may for example be on the order of about 19.5 inches. The stretched tubular article may be held at such position to accommodate maximum uniaxial stress-softening of the thermoplastic elastomeric film of the article, following which the collar may be moved upwardly to reduce the length of the distended tubular article to the value indicated in FIG. 13 as L''', which may for example be on the order of about 16.5 inches, at which point the tubular article is held and fluid such as pressurized gas or liquid is introduced into the hollow mandril 232 for subsequent radial expansion of the tubular article.

Figure 14:
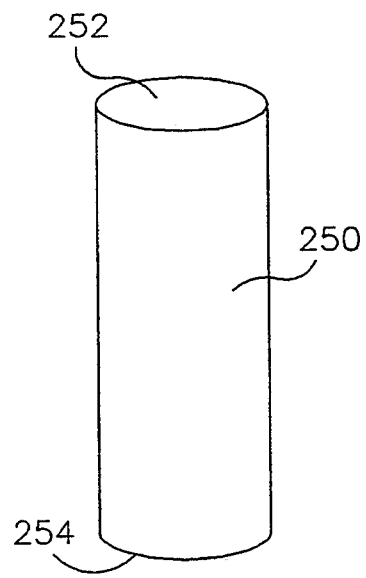
FIG. 14 is a perspective view of an expansion chamber, such as may be utilized with a mandril device of the type shown in FIGS. 10–13.

The radial expansion of the tubular article may be carried out with utilization of an expansion chamber 250 of the type shown in FIG. 14. The chambers 250 has a closed top end 252 and an open lower end 254, which may be placed over the tubular article during its extension to length L''', prior to and during pressurized fluid radial expansion of the tubular article, so that the radial expansion, and optionally axial expansion, is confined by the expansion chamber. By way of example, for a mandril unit of the type shown and described with reference to FIG. 13, the appertaining expansion chamber 250 shown in FIG. 14 may have a length of about 16 inches and a diameter of about 6 inches.

As a variant example of the mandril unit and expansion chamber shown in FIGS. 13 and 14, the mandril may be constructed such that D is 1 inch, L' is 5 inches, L''' is 15.5 inches, and L" is 17.5 inches with the appertaining expansion chamber having a length of 16 inches and a diameter of 4 inches.

Figure 15:
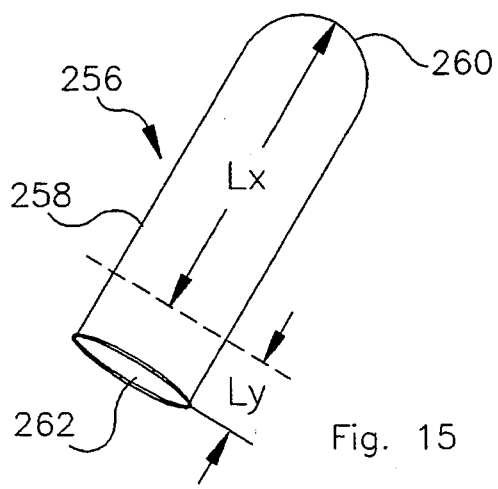
FIG. 15 is a perspective view of a stress-softened tubular article, such as may be formed using the mandril and fluid supply assembly of FIGS. 10–13, together with the expansion chamber of FIG. 14.

FIG. 15 is a perspective view of a stress-softened tubular article 256. This article comprises a generally tubular main sheath 258 which is formed of a stress-softened thermoplastic elastomeric film, with the article having been biaxially stretched with the aid of an apparatus of the type as shown in FIGS. 10–14.

The tubular article 256 has a closed distal end 260 and an open proximal end 262. The stress-softened article may have a stress-softened length $L_x$ on the order of about 8.5 inches and a non-stress-softened proximal portion of length $L_y$ which may be on the order of 1 inch (this non-stress-softened proximal portion is the area confined by the collar during radial expansion of the article, which accordingly is not stress-softened in character). The tubular article 256 is derived from an initial tubular article (native, non-stress-softened) which has a length on the mandril, as measured from the tip of the tubular article to the upper extremity of the collar on the mandril, of 7 inches, and which has been stretched in the longitudinal direction to a length of 18.5 inches and held for sufficient time to stress-soften the material, followed by relaxation of the length of the tubular article to 16.5 inches, with final gas pressurization of the article (for radial expansion thereof) in an expansion chamber having a diameter of 4 inches and sufficient length to effect expansion.

Referring again to the tubular article as shown in FIG. 15, the non-stress-softened proximal portion thereof may, if desired, be severed from the stress-softened main portion of the article, to yield a fully stress-softened product article.

After longitudinal distension and radial expansion under fluid pressure on the mandril, and subsequent relaxation of the stretching forces, the tubular article may be removed from the mandril with the form variously shown in FIGS. 7, 8, or 15, or alternatively, the stress-softened tubular article may be rolled while on the mandril, into a rolled configuration as in the manufacture of conventional latex condoms.

Figure 16:
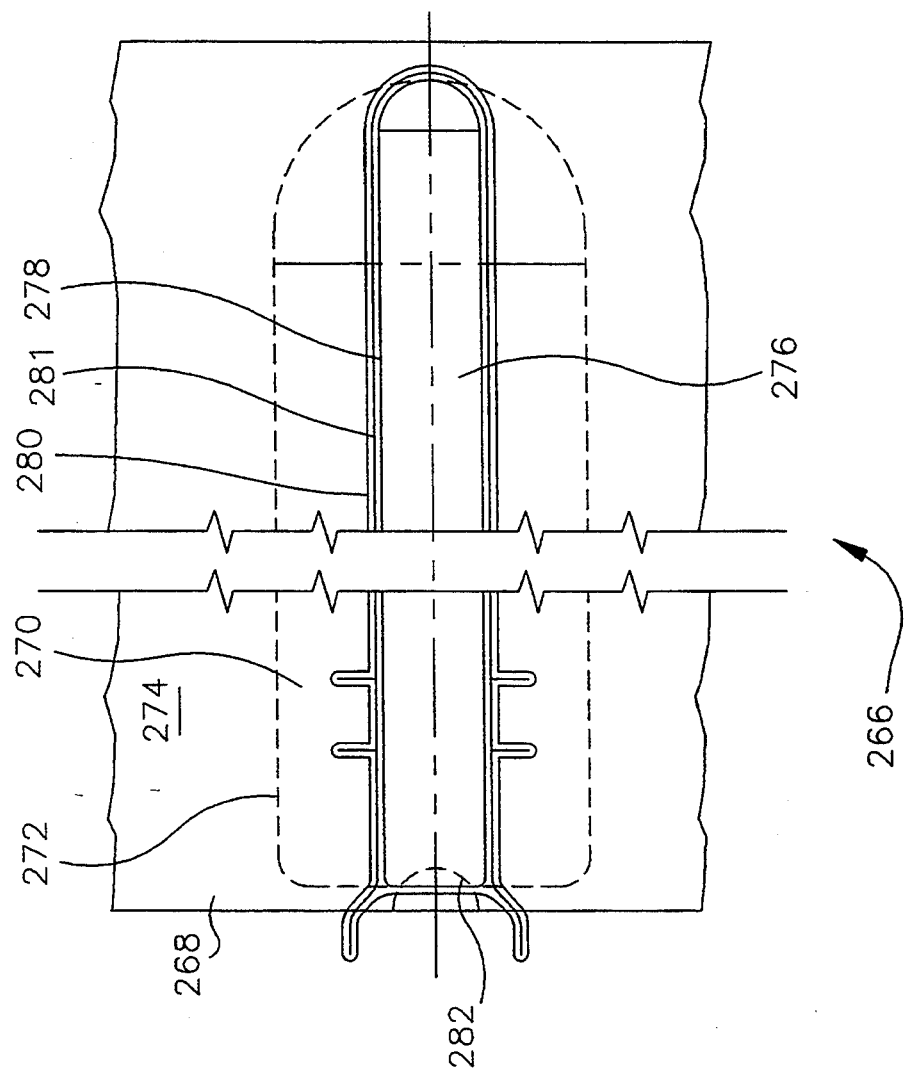
FIG. 16 is a top plan view, in section, of a mold apparatus which may be utilized to form a stress-softened tubular article in accordance with another embodiment of the present invention.

FIG. 16 is a top plan view of a half-section of a condom-forming mold assembly 266. The mold half-section 268 shown in the drawing is constructed with a cavity 270 of generally hemicylindrical shape whose boundary is indicated in dotted outline 272 in the figure. At the top face 274 of the mold half-section, an opening 276 is provided, which is bounded by edge surface 278. Line 280 defines the edge of a clamped region on the mold half-section face 274, and line 281 is a cut and seal line, indicating the locus of heat-sealing and severing of the superposed sheets of thermoplastic elastomeric material which are employed to make the condom.

The mold half-section shown in FIG. 16 is mated with a second mold section comprising a flat rubber sheet supported by a flat plate, so that the rubber sheet on the face of such plate can be brought into engagement with face 274 with mold half-section 268, with superposed sheets of thermoplastic elastomeric material clamped therebetween.

In use, two sheets of thermoplastic elastomeric material are superposed in abutting relationship to one another. These superposed thermoplastic elastomeric sheets then are positioned on the face 274 of mold half-section 268, overlying the opening 276. The planar section then is positioned on top of the thus-reposed thermoplastic elastomeric sheets, with the rubber sheet of the overlying mold section (not shown for clarity) in contact with the surface of the top sheet of the superposed pair of thermoplastic elastomeric sheets. The superposed sheets thus are clampingly held between the respective mold half-sections, with a pressurizing air tube or other means (not shown) being inserted between the rubber sheet of the overlying mold section and the top sheet of the superposed sheet array to introduce pressurized fluid between the sheets whose edges are clamped (the clamped portion being demarcated by clamping edge line 280).

Such introduction of pressurized fluid between the overlying mold section and the superposed sheets effects expansion of the superposed sheet array into the mold cavity 270 of the mold half-section 268, so that the sheet array is radially outwardly distended until it comes in contact with the edge of the cavity 270 at line 272.

Contemporaneously, heat-sealing means, such as a heat-sealing wire disposed along line 281 (not shown in FIG. 16 for clarity) is actuated, as for example by electrical resistance heating thereof, to heat-seal and concurrently sever the heat-sealed film at line 281. Both thermoplastic elastomeric sheets thus are stretched into the same die cavity in the lower mold half-section, thereby assuring that the heat-sealed seam will be on an axis of symmetry of the condom. The resulting expanded, stress-softened array of superposed sheets then is deflated by terminating the flow of pressurized fluid, following which the resulting heat-sealed and stress-softened condom may be removed from the mold, by separation of the sections thereof and extraction of the product condom from the cavity defined by the mated mold sections.

Alternatively, the condom may be formed in an unexpanded state by the heat-sealing and severing operation just described, with the heat sealing of the proximal end of the condom, followed by cutting of a hole indicated by dotted line 282, in the proximal portion of the condom. In this manner, there is formed a proximal opening of reduced diameter as compared to the diameter of the main sheath portion of the condom, so that an annular sealing element is integrally formed with the condom in the manufacturing operation, to yield a condom having an annular sealing element as more fully described in U.S. Pat. No. 4,964,416 of Robert. G. Wheeler, the disclosure of which hereby is incorporated herein by reference.

Figure 17:
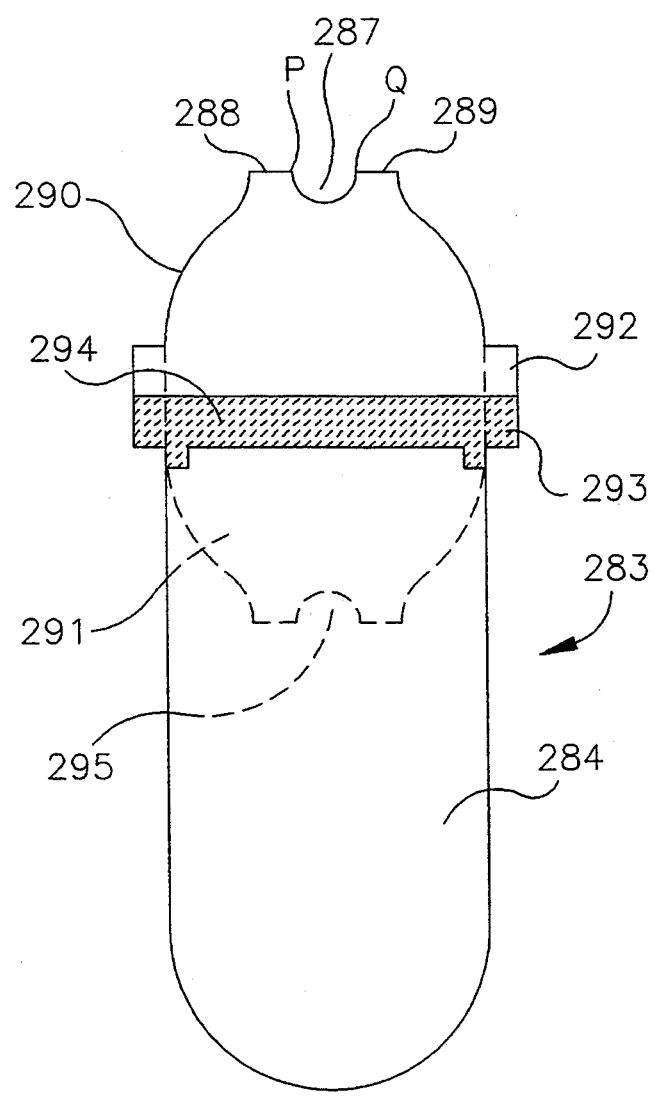
FIG. 17 is a side elevation view of a stress-softened tubular article according to another embodiment of the invention, showing the shape of a sealing structure in the interior volume of the tubular article, as represented in dotted outline.

FIG. 17 is an elevation view of a condom 283 formed by the method described with reference to FIG. 16. The condom 283, as shown, includes a main sheath portion 284 having a closed distal end 285, and a proximal portion 286 having a proximal opening 287 between the rear extremities 288 and 289 of the sheath. The sheath 284 is perimetrally sealed along its entire edge 290 from point P at the edge of proximal opening 287 around the entire exterior edge of the condom, with the edge seal extending forwardly from point P to the distal end, around the distal end, and then rearwardly to point Q bounding proximal opening 287 at a point opposite point P. In this manner, the heat-sealed sheets forming the sheath define an interior volume whose only ingress is through proximal opening 287.

Subsequent to formation of the condom 283 as shown in FIG. 17, the proximal portion 286 of the condom may be reentrantly disposed in the interior volume of the condom, by tucking the proximal portion 286 into the part of the sheath 284 anterior to such proximal portion, so that the proximal portion 286 then becomes the reentrant portion 291 shown in dotted line representation in FIG. 17. Concurrently with such inverting and subsequent interior disposition of the proximal portion 286, the lateral flange 292 is tucked into the corresponding portion of the flange 293 anterior thereto. At this point, a tongue member or other separation element is inserted into the reentrant proximal portion 291, and the resulting band 294 of double thickness above and below the separation element is heat-sealed in the hatched area illustrated in dotted line representation, to form a posterior border for the resulting condom, with the reentrant portion 291 providing an annular sealing element with a central opening 295, through which the penis of a wearer is inserted into the interior volume of the condom when the condom is donned for use. In this manner, the circumscribing edges of the opening 295 of the proximal portion 291 bear compressively against the penis of the wearer, to provide a sealing function enhancing the safety and reliability of the condom article.

Figure 18:
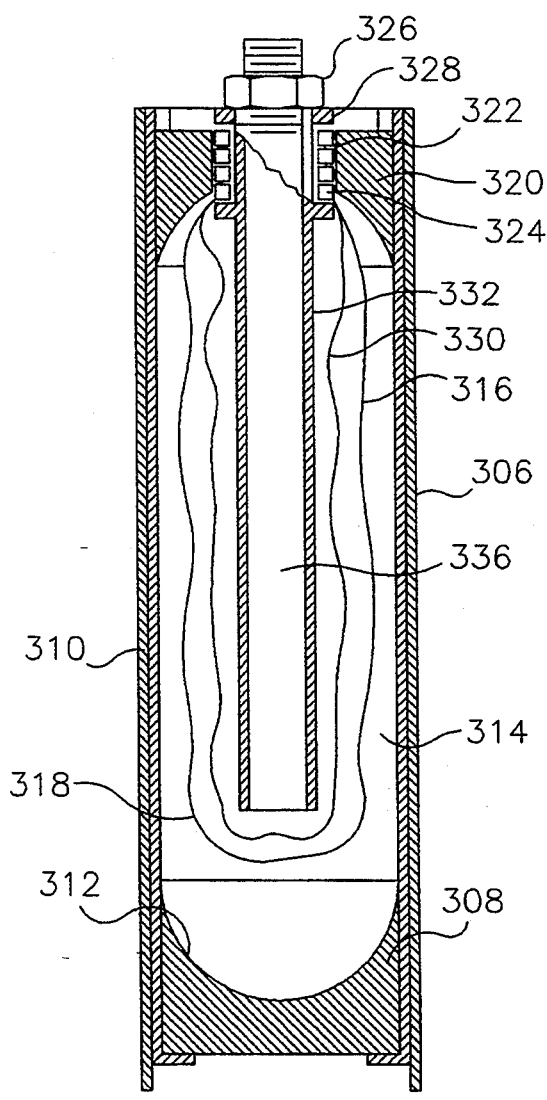
FIG. 18 is a partially sectioned, partially broken away view of an apparatus for thermoforming and stress-softening tubular articles, according to yet another embodiment of the invention.
Figure 19:
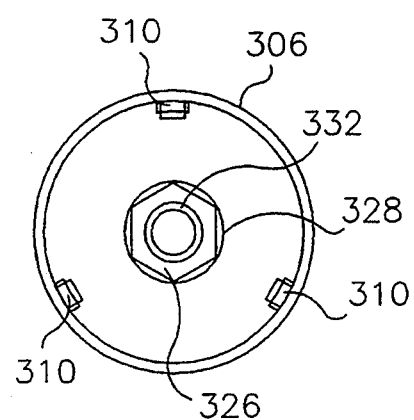
FIG. 19 is a top plan view of the FIG. 18 apparatus.

FIG. 18 is a cross-sectional, elevation view, and FIG. 19 a top plan view, of a heat-sealing and thermoforming apparatus for making condoms.

The apparatus comprises an outer cylindrical shell 306 joined at its lower portion to end block 308, by means of straps 310, to allow loose fitting of the end block 308 to the cylindrical shell 306. The end block 308 suitably is formed with a concave contour 312 approximating the frontal contour of the condom to be formed.

In the interior volume 314 defined by the cylindrical shell 306, there is disposed a pouch 316 of extruded or heat-sealed tubular film with a heat-sealed closed distal end 318.

At the upper portion of the cylindrical shell 306 is interiorly mounted a second end block 320 having a central cylindrical passage 322 therein. Disposed in passage 322 is a compression stopper which is diametrally expandable by tightening nut 326 against washer 328.

A balloon 330, formed of a suitable material such as latex, is reposed interiorly of the tubular film pouch 316. The respective necks of the balloon 330 and the tubular film pouch 316 are compressed between the inner wall surface of cylindrical passage 322 of the end block 320, and the compression stopper 324.

The neck of the balloon 330 is cemented or otherwise affixed permanently to the compression stopper 324. A central tube 332 is interiorly disposed in the balloon 330 and acts as a mandril for the compression stopper 324. The tube 332 also provides an air inlet, being open at its lower end, for inflating the inner balloon and outer thermoplastic tubular film. The upper end of this tube is connected to a selectively controllable source of pressurized gas (not shown for clarity).

In use, the tubular film pouch 316 is pulled over the balloon 330 and the compression stopper 324. The stopper and attached pouch then are placed in the assembly as shown in FIG. 18, and the balloon and pouch are sealed by compressing the compression stopper, via tightening of the compression nut 326. The pouch 316 then is inflated, by introducing air or other pressurizing gas into the balloon from gas flow passage 336 of tube 332, as for example air at a pressure of 1-3 psig.

The entire assembly as illustrated in FIG. 18 then is placed in an elevated temperature medium, such as boiling water or an oven at a sufficient thermoforming temperature. After adequate exposure to the elevated temperature conditions, which may for example involve an exposure time on the order of 0.5 to 3 minutes, the assembly is quenched in a suitable quenching medium such as water at ambient temperature, or by air blast exposure to air at ambient temperature.

The forming assembly then is disassembled, and the thermoplastic condom, produced by expansion of the pouch 316 to conform to the interior shape of the cylindrical shell 306 and the interior contours of the end blocks 308 and 320, is removed from the compression stopper after it has been loosened and contracted to a suitable diametral extent allowing for removal of the finished condom. Thus, a condom is formed which has assumed the shape of the interior bounding surfaces of the thermoforming assembly, and which has a reduced diameter neck to facilitate retention of the condom on the penis of a wearer in use.

Figure 20:
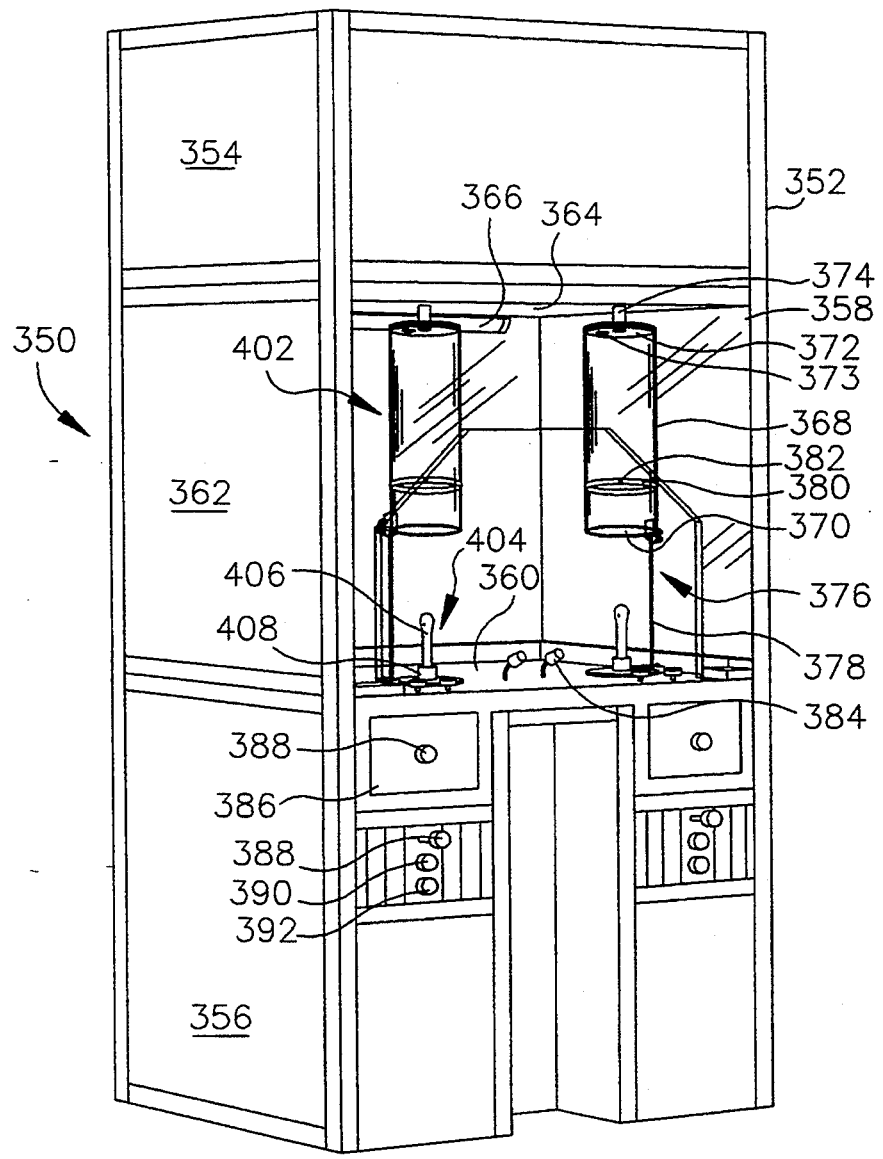
FIG. 20 is a perspective view of an apparatus for stress-softening a tubular article formed of a thermoplastic elastomeric material and having a closed first end and an open second end.

FIG. 20 is a perspective view of an apparatus 350 for stress-softening a tubular article formed of a thermoplastic elastomeric material and having a closed first end and an open second end. This starting work piece article is sometimes herein referred to as a "condom precursor", "condom blank", or "condom starting article."

The apparatus 350 comprises a cabinet or housing 352, including upper and lower support portions 354 and 356, respectively, together with an intermediate work station portion 358.

The intermediate work station portion 358 includes a base or support surface 360, on which is reposed mandril assembly 404, comprising mandril 406 and base support structure 408. The mandril assembly 404 is associated with a hollow cylindrical housing 402, thereby forming with the mandril assembly a coaxially arranged stress-softening unit of the overall apparatus. It will be noted that the intermediate work station portion of the apparatus comprises side-by-side work station housing/mandril assemblies. For ease of description, only the left-hand housing/mandril assembly will be described, it being understood that the apparatus is symmetrically constructed with respect to such assemblies.

The intermediate work station portion 358 may be enclosed by transparent walls 362 on its sides and back portion, and optionally at its front to form a completely enclosed work space in which the stress-softening operation can be observed. The upper and lower facilities portions 354 and 356 of the apparatus contain the necessary piping, instrumentation, controls, power supply means, etc., as required for the operative apparatus.

At the top of the intermediate work station portion 358 is a sealing partition 364 dividing the intermediate work station portion from the upper facilities portion 354. Mounted on partition 364 is a light fixture 366 for providing illumination to the work space of the intermediate portion, it being understood that fixture 366 is operatively connected to suitable power supply means, e.g., a battery, or power cord means which extend exteriorly of the apparatus housing 352 for plug-in to a suitable electrical power outlet (such power supply arrangement not being shown for purposes of clarity).

The mandril 406 is disposed on support 408 so that the axis of the mandril is vertically arranged. The mandril, as shown and as further described hereinafter, is of generally cylindrical shape, including a cylindrical main shaft portion and a smooth bulbuous head or distal portion.

The mandril 406 extends through the base 408 into the interior volume of lower facilities portion 356 of the housing 352, and is operatively connected with means for selectively longitudinally translating the mandril along its central vertical axis between a first installation position, as shown in the drawing, and a second expansion position thereabove. The mandril 406 thus is selectively reciprocatingly raiseable and lowerable along the direction of its vertical axis.

The cylindrical housing 402 is arranged such that its own central axis is vertically aligned and coincident with the longitudinally extending central vertical axis of mandril 406, such that the housing 402 and mandril assembly 404 are coaxially arranged. The cylindrical housing comprises a bounding wall 368 defining an interior space 370 within the housing. The housing constitutes a confining means within which the precursor tubular article can be stress-softened. Such confining means may alternatively comprise a housing of non-circular or other shape (in cross-section). Further, the confining means need not be of a continuous solid character as in the case of the cylindrical housing 402. Instead, the confining means could suitably comprise a netting or other foraminous or discontinuous structual means. A confining means comprising netting could be usefully employed to additionally provide texturing of the film, and the confining means could otherwise be suitably constructed to impart a particular pattern, design, or other surface conformation(s) to the film being stress-softened.

Returning to the illustrative embodiment shown in FIG. 20, the housing wall 368 at its upper end leak-tightly mates with a closure member 372 which in turn is joined to a vertically extending shaft member 374 extending into the upper facilities portion 354 of the cabinet 352. Closure member 372 features gas displacement openings 373 therein, to permit expansion of the precursor tubular article in the housing during stress-softening inflation thereof. At its lower portion, the housing wall 368 has exteriorly joined thereto a displacement assembly 376 comprising a shaft 378 extending into the lower facilities portion 356 of the apparatus, in which the shaft 378 is joined operatively joined to means for selectively longitudinally translating the housing between a first retracted position, as shown, in which the cylindrical housing is in longitudinally displaced relationship to the distal end portion of the mandril 406, and a second engaged position at which the housing wall lower extremity engages the base 408 of the mandril assembly so that the mandril is disposed in the interior volume 370 of the housing 402. Thus, the housing 402 is selectively reciprocatable between the raised position shown in FIG. 20 and a lower position at which the lower edge of the housing wall 368 is in leak-tight engagement with the base 408 of the mandril assembly 404. During such translation, the shaft 374 correspondingly translates and passes through the sealing partition 364 through a suitable receiving opening, with the shaft 374 being journaled in suitable bearings or otherwise secured in the upper facilities portion 354 of the apparatus in a manner allowing free translation in response to the operative translation means associated with shaft 378.

Secured within the interior volume 370 of housing 402 is a collar member 380 which is secured to the wall by means of suitable mechanical fasteners 382. The purpose of collar 380 is to leak-tightly engage with the base 408 of the mandril assembly 404. Thus, there is provided a double leak-tight seal for the mating of the housing with the base 408 of the mandril assembly, including a leak-tight contact between the lower end of housing wall 368 and the base, and leak-tight juncture of the collar 380 with the base, as will be described more fully hereinafter with respect to FIGS. 21-25.

Associated with the translation means for selectively and reciprocatingly translating the housing 402 between an upper raised position and a lower engaged position are means for actuating the mandril translating means when the housing 402 engages the base 408 of the mandril assembly 404, and effecting subsequent translation of the mandril to its second (raised) expansion position.

The various translating means and actuating means associated with the housing and mandril assembly have not been illustrated for clarity in FIG. 20, but may readily be constructed and suitably operatively arranged, within the skill of the art and without undue experimentation.

Mounted on the floor 360 of the intermediate work station portion 358 is an internal pressure gauge 384, the purpose of which is to monitor pressure in the interior of the condom blank as it is being expanded for stress-softening thereof to produce a final stress-softened condom article. The nature and purpose of this monitoring of pressure will be more fully apparent from the ensuing discussion of FIGS. 21-25.

The lower facilities portion 356 of the apparatus features a control panel 386, featuring a vacuum control light 388 for monitoring and control purposes, together with a condom blank pressurizing switch 388 for initiating pressurization of the condom blank for stress-softening thereof, together with a blow pressure gauge 390 for monitoring the gas pressure of gas introduced into the interior volume of the condom blank for pressurization and expansion of same. Finally, the control panel 386 comprises a pneumatic switch 392, the purpose of which is to initiate the translation-actuation sequence as hereinafter described.

Figure 21:
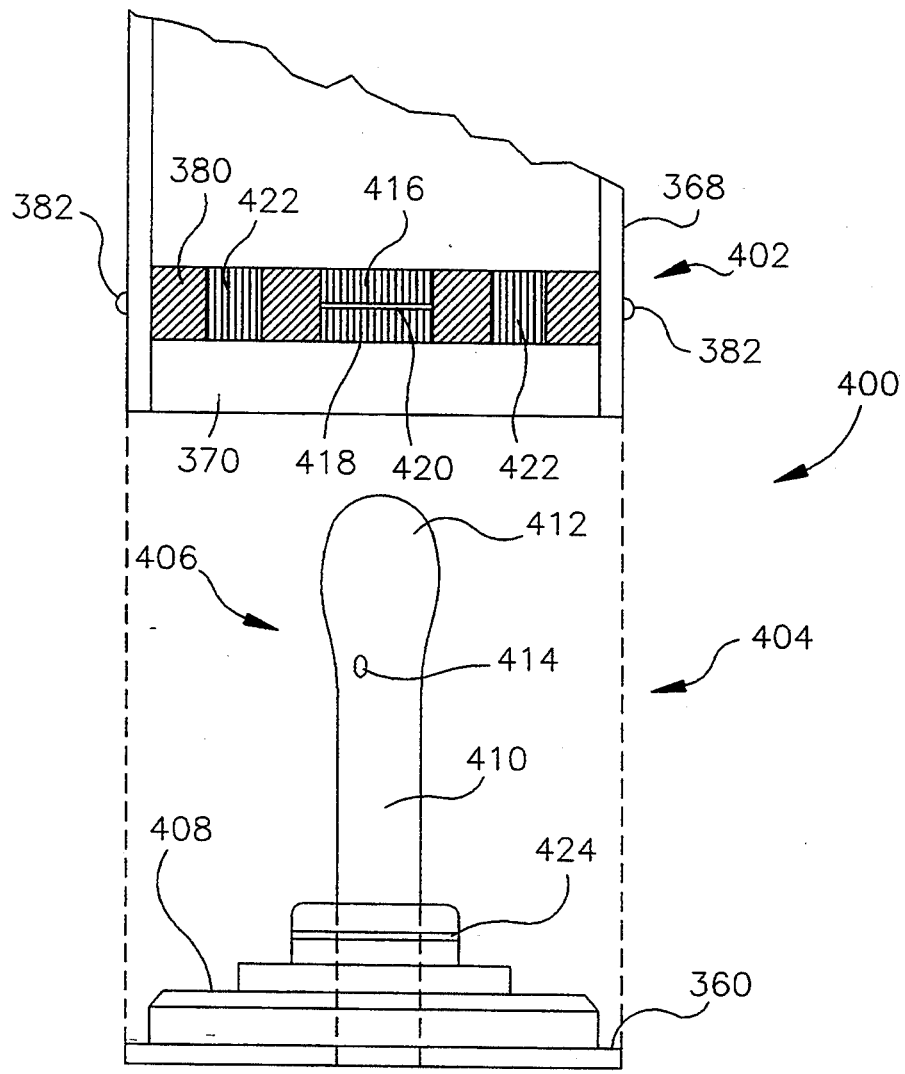
FIG. 21 is a front elevation view of the mandril and housing assembly of the FIG. 20 apparatus.

FIG. 21 is a front elevation view of the mandril and housing assembly of the FIG. 20 apparatus. As shown, the mandril assembly 404, comprising mandril 406 and base 408, is reposed on floor 360 of the overall assembly (see FIG. 20).

The mandril 406 comprises a main cylindrical shaft portion 410 and a bulbous head or distal portion 412.

Below the bulbous distal end 412 of the mandril 406 in the vicinity of the juncture of the main cylindrical shaft 410 and bulbous distal end 412 is a gas flow passage 414, which communicates with a hollow interior space (not shown) within mandril 406, and communicating with pressurized gas delivery means disposed in the lower facilities portion 356 of the overall apparatus (see FIG. 20). The shaft 410 of the mandril extends downwardly through the base 408 of the mandril assembly, as shown and is operatively connected with the aforementioned translation/actuation means whereby the upward translation of the mandril from the first installation position shown to the second expansion position, and back again to the first installation position after the stress-softening processing is completed. Such translation and actuation means are not shown for purposes of clarity, but as mentioned, as within the skill of the art insofar as their construction and operation as concerned.

Overlying and coaxially arranged with respect to the mandril assembly 404 is the housing 402, the lower portion of which is shown. The housing 402 comprises cylindrical wall 368 bounding the interior space 370 of the housing. The collar 380 is joined to the wall 368 by suitable fastening means 382, e.g., fastening screws, or the like.

Figure 22:
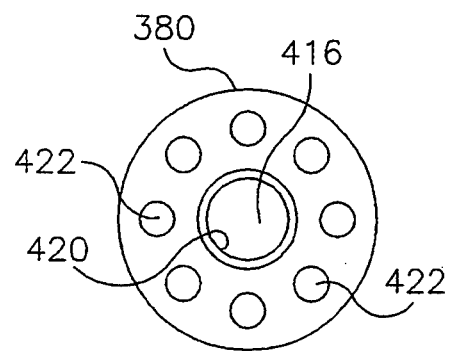
FIG. 22 is a top plan view of the collar element which is disposed in a lower portion of the housing of FIG. 21, for mating with the mandril sub-assembly.

The collar 380 may be formed of any suitable material, and is shown in top plan view in FIG. 22, wherein all reference correspond to those employed in FIG. 21.

As best shown in FIG. 22, the collar 380 features a main central opening 416, the bounding surface 418 of which is circumscribed by a 0-ring at its central region. The 0-ring 420 may suitably be disposed in a receiving groove, or other secured to the bounding wall surface of the central opening 416.

Radially outwardly displaced from the central collar opening 416 and circumferentially uniformly spaced apart around the periphery of the annular collar are openings 422, the purpose of which is to facilitate gas removal from the interior volume 370 of the housing 402, concurrent with introduction of pressurizing gas into the interior volume of the condom blank, through gas flow opening 414 in mandril 406.

The base 408 of the mandril assembly 404 features an 0-ring 424 which coacts with O-ring 420 of the collar 380 to effect sealing when the housing 402 is lowered from the position shown in FIG. 21 so that the lower extremity of wall 368 engages floor 360 of the base 408 of the mandril assembly. Prior to this engagement, a condom blank is mounted on mandril 406, with the closed distal end of the condom blank reposing on bulbous distal end 412 of the mandril, and the main tubular sheath portion of the condom blank depending downwardly therefrom over the shaft 410 of the mandril.

The condom blank-bearing mandril 406 then passes through central opening 416 of the collar as the housing 402 is lowered to the engagement position, with the O-ring 420 finally engaging 0-ring 424 of the base 408 of the mandril assembly. At such point of engagement, the open proximal end of the condom blank is clamped between the collar and the base of the mandril assembly, and gas introduction is initiated, whereby pressurized gas, e.g., air, is flowed through gas flow opening 414 into the interior volume of the condom blank mounted on mandril 406, contemporaneously with upward translation of the mandril from its first installation position to the second expansion position. Alternatively, the mandril may be longitudinally translated prior to initiation of gas flow, or the two events may take place in any other desired arrangement or sequence.

Regardless of the specific sequence of such events, the condom blank is contemporaneously longitudinally stretched and is radially outwardly expanded to effect stress-softening of the condom blank to produce a stress-softened condom product article.

Concurrently with the introduction of pressurized gas through gas flow opening 414 in the mandril, gas already with the housing 402 may be withdrawn through gas withdrawal openings 422, by coupling same to means such as a vacuum pump or reversed blower, so as to evacuate the interior volume 370 of the housing 402, to thereby increase the pressure differential across the film of the condom blank and to faciliate expansion and stress-softening of the condom blank.

Although illustratively described as involving concurrent pressurized gas introductions through the gas flow opening 414 and withdrawal of gas from the housing through gas withdrawal passages 422, it will be appreciated that in some instances, only pressurized gas introduction through gas flow opening 414 needs to be effected, and that in such instance openings 422 in collar 380 may serve simply as venting openings whereby gas in the interior volume displaced by the expansion of the condom blank therein is able to be freely vented.

The aforementioned operation of the mandril and housing are more fully explained with reference to FIGS. 23–25. FIG. 23 is a front elevation view of the mandril and housing assembly of the FIG. 20 apparatus, with the housing in a first retracted position, and with the mandril in the first installation position.

FIG. 24 is a front elevation view of the mandril and housing assembly of FIG. 23, after the housing has been longitudinally translated to an engaged position, and the tubular article has been expanded by flow of pressurized gas through the mandril (gas flow opening) into the interior volume of the tubular article.

FIG. 25 is a front elevation view of the FIG. 24 mandril and housing assembly, after the pressure of the gas flow into the interior volume of the expanded tubular article has been released, and the tubular article has deflated onto the mandril, with the housing retracted to its initial position corresponding to that shown in FIG. 23.

Referring now to FIG. 23, a condom blank 450 is shown disposed on the mandril, with the closed distal end of the condom blank reposing on bulbous distal end 412 of the mandril, and the main cylindrical sheath of the blank depending downwardly over the cylindrical shaft 410 of the mandril. The housing 402 is shown in its first retracted positioned, as joined by a sequence actuator 452 to reciprocatable shaft 378. At the lower end of the shaft 378 is associated a switch 454 for initiation of the pressurizing sequence.

Accordingly, the pneumatic switch 392 on the lower facilities portion of the apparatus (see FIG. 20) is initially depressed, which results in housing 402 being lowered on shaft 378 until engagement is achieved between the housing and the base 408 of the mandril structure, as shown in FIG. 24. At this engagement position, the switch initiator 452 contacts the switch 454 to initiate delivery of pressurized gas into the mandril for discharge into the interior volume of the condom blank through gas flow opening 414. Contemporaneously, as for example prior to and during such gas flow introduction, the mandril is vertically upwardly translated along its longitudinal axis to longitudinally stretch the condom blank, with the mandril at its uppermost extension being in the position shown in FIG. 24. After the mandril has been translated to its uppermost extent continuing introduction of gas through the gas flow opening 414 will result in further axial expansion of the condom blank 450 above the bulbous distal end 412 of the mandril, as shown in FIG. 24.

Subsequent to the expansion of the condom blank in the longitudinal and radial directions, the flow of pressurized gas into the condom blank is terminated, and the expanded condom blank is allowed to deflate loosely onto the mandril, as the housing thereafter is vertically upwardly translated away from the mandril to its original retracted position, to the position shown in FIG. 25. The resulting stress-softened condom article 460 on the mandril then may be removed therefrom, either manually or automatically (such as by pneumatic and/or mechanical removal means) and the product article then is passed to further processing and/or packaging operations. In some instances, it may be desired to reverse roll the stress-softened condom article on the mandril to a conventional rolled form for subsequent use. In other instances, it may be desirable to maintain the distal tip of the stress-softened condom in contact with the bulbous distal end 412 of the mandril, as for example by drawing vacuum on the mandril so that the distal end of the condom is suctioningly held on the bulbous distal end of the mandril, to facilitate subsequent eversion of the condom and further processing thereof, e.g., for subsequent packaging.

Alternatively, it may be desired to attach a ring to the condom as an elastic filament around the open proximal end of the condom, or to otherwise treat or process the condom article to facilitate or enhance its subsequent packaging and/or use.

Figure 26:
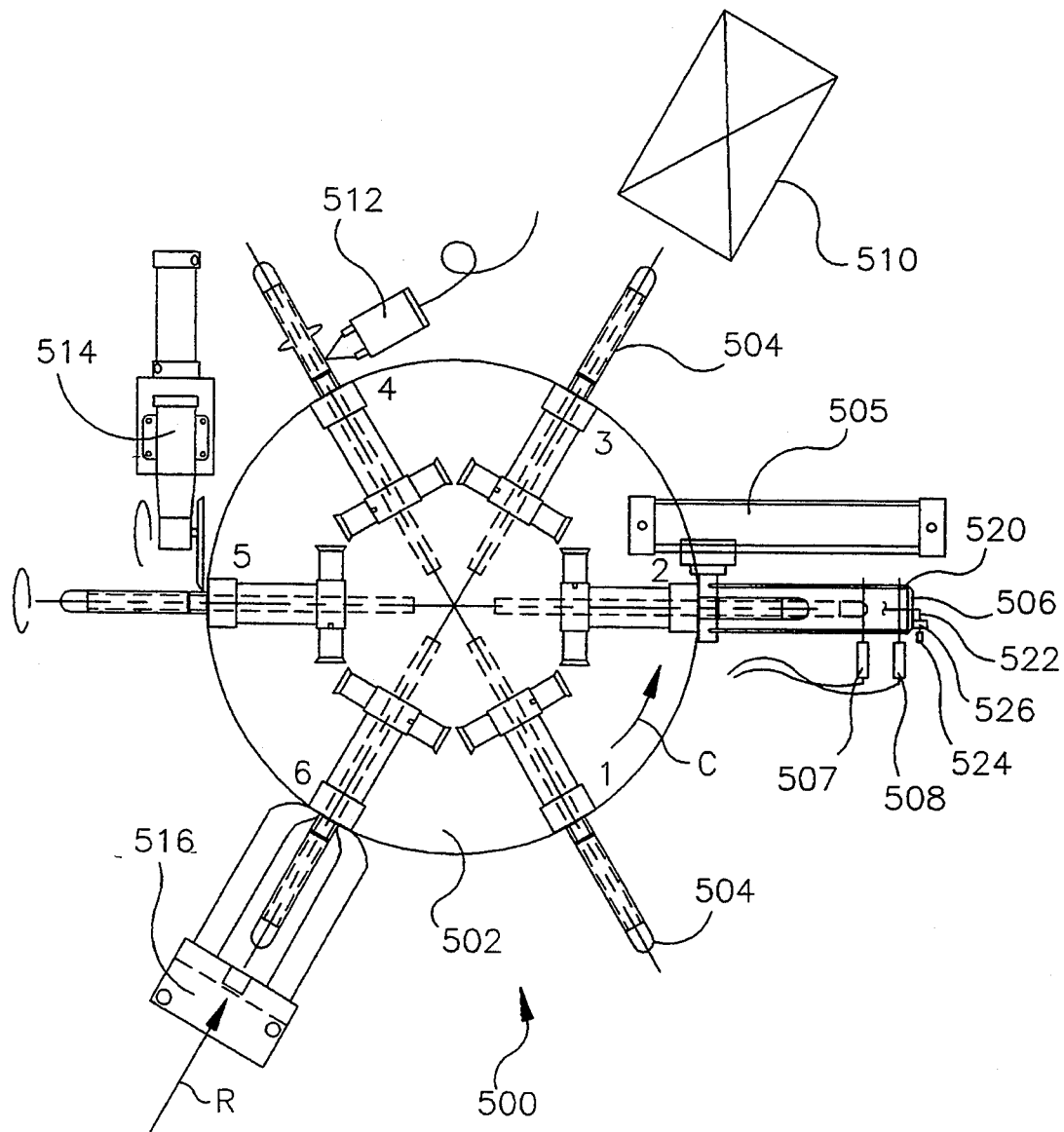
FIG. 26 is a top plan view of a multi-station apparatus for forming stress-softened condoms.

FIG. 26 is a top plan view of a multiple station apparatus for forming blow-softened condom articles.

The apparatus 500 comprises an index table 502, which may for example comprise a 12-station Geneva drive stop-motion index table, which is arranged for counterclockwise rotation as indicated by arrow C.

The index table 502 is numbered as to its constituent stations 1–6.

As shown, station 1 features a mandril 504 which is disposed at an operator loading position, whereby a condom blank—i.e., a non-stress-softened precursor tubular article having a closed distal end, an open proximal end, and a main cylindrical sheath—can be manually or automatically mounted on the mandril 504.

Once installed, the condom blank on the mandril is rotated to the blow-softening station 2. At station 2, the rodless cylinder 505 translates a housing 506 over the mandril bearing the condom blank. The mandril then is radially outwardly extended to a maximum extended position, indicated in FIG. 26 in dotted outline, in the interior space of housing 506.

At the maxiumum extended position of the mandril, pressurized gas is introduced through the mandril (which may comprise suitable gas flow openings, as previously described) into the condom to effect radial and longitudinal expansion thereof.

Subsequently, at the maximum extent of expansion of the condom blank, the distal tip of the condom comes into contact with lever 520 having a frontal disc or flange which abuts the expanded condom.

The lever 520 is joined to a sensor arm 522 which at its opposite end is counterweighted with weights 524. The sensor arm 522 is mounted on a rotor sensor assembly 526, which is operative to detect movement of the lever 520 and sensor arm 522 coupled therewith.

By means of the lever, sensor arm, and rotor sensor assembly, the leak-tightness of the expanded condom blank can be determined. Thus, if the condom blank contains pinholes or other structural discontinuities, the resulting leakage will result in deflation of the condom blank, and corresponding movement of the lever and sensor arm. Such movement will be sensed by the rotor sensor assembly, which in turn identifies the leaking condom blank as a reject article, which will be discharged from the apparatus at the next station, as subsequently described.

Alternatively, the leak-tightness of the expanded condom blank may be determined by an arrangement of sensors, such as the optoelectronic sensors 507 and 508 illustratively schematically shown in FIG. 26. This pair of sensors can be appropriately positioned, so that any deflation of the expanded condom is sensed by such means, and the condom blank then will be rejected at the next, or a subsequent, station of the apparatus.

Such leak-tightness testing means may be associated with a suitable relay or other control and instrumentation means whereby the fully inflated condom is held at a full inflation pressure for a predetermined period of time, e.g., one second, to facilitate the determination of reject or non-reject status of the inflated condom.

The sensors 507 and 508 may be powered by any suitable power supply means (not shown) and may be incorporated in a unitary sensor head, rather than being structurally discrete as illustratively schematically shown. The rodless cylinder 505 which reciprocates the housing 506 from its inner engaged position and its outer disengaged position may be of any suitable type well known in the art, as for example a 1.5 inch inner diameter Bimba rodless cylinder unit with a 24-inch stroke.

Subsequent to the stress-softening of the condom blank, the tubular article is depressurized, the mandril retracts, and the housing 506 is retracted by the rodless cylinder 505.

The index table then rotates the stress-softened tubular article to station 3, where any reject condom articles are discharged from the mandril into a waste receptacle 510, by pneumatic blowoff of the rejected article from the mandril 504.

Assuming that the stress-softened tubular article is a non-reject article, the stress-softened tubular article then moves on mandril 504 to station 4. At station 4, a hot foam gun 512 applies a coating of hot foam material to the proximal region of the stress-softened tubular article, as the mandril is rotated to accommodate such application. The hot foam material may be of any suitable type, which on cooling dries to a solid form and forms a discrete ring or band on the condom, to bound the proximal end opening thereof and to form an element for rolling of the condom in a conventional manner. Alternatively, instead of the hot foam gun 512, station 4 may accommodate manual or automatic installation of a ring or filament of resilient material to the proximal region of the tubular article, or other elements or treatments may be effected to provide a ring or other element on the proximal portion of the tubular article (e.g., curing of a pre-applied foam or tacky ring material condom to facilitate rolling and to bound the proximal end opening of the ultimate tubular product article.

After processing at station 4, the indexing table 502 is rotated so that the tubular article at station 5 is cut at its proximal end by cutter device 514, so that the non-stress-softened portion of the tubular article (the "neck" or "collar" portion of the tubular article) is trimmed away so that the proximal end of the main sheath portion is trimmed to the vicinity of the applied ring, with the cutter device 514 being actuated while the mandril 504 is rotated at station 5.

Subsequent to such proximal end trimming at station 5, the index table 502 is rotated to station 6, at which roll-up unit 516 is translated inwardly (in the direction of arrow R) into engagement with the base (proximal end) of the condom, with such roll-up means thereafter effecting rolling of the condom into a fully rolled form. The fully-rolled condom resultingly disengages from the mandril and is conveyed to packaging or further downstream processing steps.

It will be recognized that the multi-station apparatus illustratively shown may be substantially modified, to accommodate specific condom-forming unit operations of the overall process, as comprising stress-softening of the condom. For example, it may be desirable in some instances to consolidate the formation or provision of a ring or other augmentation structure to the proximal end of the condom, concurrently with its trimming, so that the unit operations illustratively shown at stations 4 and 5 of the apparatus could be consolidated into a single station of the apparatus.

Further, it will be recognized that a wide variety of index tables exists, and that index tables having greater or lesser numbers of positions, relative to the illustrative 12-station index table, may advantageously be employed in the broad practice of the invention.

By means of the multiple station apparatus 500 shown in FIG. 26, it is possible to accommodate mass production of stress-softened condom articles according to the present invention.

The features and advantages of the present invention are more fully shown by the following non-limiting examples.

EXAMPLE I

In this test, samples of UO73 polyurethane thermoplastic elastomer film (BASF Corporation, Parisippany, N.J.) were tested in non-stress-softened form and in stress-softened form, at film thicknesses of 40 micrometers original thickness and 50 micrometers original thickness (the stress-softened samples were of course reduced in thickness from such initial values by the stress-softening thereof). Tensile testing was carried out with an Instron ® test machine, and strain distance, in millimeters, was measured, together with force, thickness, and tensile strength, in English and metric units, as set out below in Table I.

Comparing non-stress-softened Samples Groups A and B (40 micrometer initial film thickness) with Samples Groups C and D for corresponding stress-softened films, show that the stress-softened films exhibited sig-

TABLE I

| Samples Group | Force N | lbs. | Thickness mm | inches | Tensile MPa | Psi | % Elong. | lbs Force | Tear Resistance, Pli |
|---|---|---|---|---|---|---|---|---|---|
| A | 31.58 ± 6.01 | 7.10 ± 1.35 | 0.036 ± 0.003 | 0.0014 ± 0.0001 | 44.17 ± 7.46 | 6392 ± 1118 | 431 ± 32 | 0.775 ± 0.083 | 1083 ± 57 |
| B | 32.14 ± 6.18 | 7.23 ± 1.39 | 0.036 ± 0.001 | 0.0014 ± 0.0001 | 44.27 ± 8.79 | 6402 ± 1372 | 425 ± 24 | 0.769 ± 0.070 | 1025 ± 93 |
| C | 19.12 ± 3.65 | 4.30 ± 0.822 | .025 ± 0.003 | .001 ± 0.0001 | 38.72 ± 5.96 | 5581 ± 887 | 307 ± 29 | 0.171 ± 0.096 | 933 ± 106 |
| D | 20.33 ± 5.26 | 4.57 ± 1.18 | .025 ± 0.003 | .001 ± 0.0001 | 41.41 ± 11.23 | 6025 ± 1623 | 315 ± 15 | 0.421 ± 0.08 | 92.5 ± 164 |
| E | 55.29 ± 12.30 | 12.43 ± 2.76 | 0.049 ± 0.002 | 0.0017 ± 0.0001 | 56.73 ± 12.20 | 8208 ± 1734 | 488.5 ± 37 | 0.768 ± 0.087 | 1045 ± 117 |
| F | 49.57 ± 8.28 | 11.14 ± 1.86 | .047 ± 0.002 | 0.0019 ± 0.0001 | 52.57 ± 8.80 | 7615 ± 1268 | 473 ± 25 | 0.884 ± 0.088 | 1082 ± 96 |
| G | 29.36 ± 13.8 | 6.60 ± 3.12 | .030 ± 0.001 | .0012 ± 0.0001 | 48.79 ± 23.34 | 6901 ± 3337 | 269 ± 74 | 0.529 ± 0.09 | 895 ± 138 |
| H | 37.96 ± 7.58 | 8.53 ± 1.70 | 0.031 ± 0.002 | .0012 ± 0.0001 | 61.66 ± 12.89 | 8849 ± 1876 | 331 ± 36 | 0.538 ± 0.104 | 923 ± 143 |

Table I also tabulates the percent elongation for such tensile testing, and the absolute force, in pounds, required to effect such elongation. Finally, the samples are tabulated for thickness, in inches, and tear resistance in units of pounds per linear inch (pli). Each of the values set out in the table below was an average of a number of samples, with two separate runs being carried for each sample. For ease of reference, the sample Groups A-H tabulated in Table II are identified below with respect to the number of samples and initial film thickness for each:

Samples Group A represented 5 samples each of which was submitted to 2 runs, with an initial film thickness of 40 micrometers and with the film samples being non-stress softened.

Samples Group B utilized 5 samples of 2 runs each, at an initial film thickness of 40 micrometers, and with the films being non-stress-softened in character (Sample Groups A and B were identical except that the film stock used for the samples was from a different lot in each Group).

Sample Group C represented 7 samples of 2 runs each, at a 40 micrometer initial film thickness, with the samples being stress-softened by air expansion utilizing a stress-softening procedure and apparatus as generally shown and described with reference to FIGS. 10–15 herein.

Samples Group D was based on 7 samples each having 2 runs, for a same type material as for Samples Group C, but a different film stock lot.

Samples Group E was based on 5 samples with 2 runs each, for 50 micrometer initial film thickness films of non-stress-softened polyurethane material.

Samples Group F was based on 5 samples with 2 runs each, for 50 micrometer initial film thickness films of non-stress-softened polyurethane material, of a different lot than the films used in Samples Group E.

Samples Group G was based on 5 samples with 2 runs each, of a 50 micrometer initial film thickness polyurethane material which had been blow-softened in the same manner as the samples of Samples Group C.

Samples Group H was based on 5 samples with 2 runs each, for 50 micrometer initial film thickness polyurethane films which were blow-softened in the same manner as the samples of Samples Group D.

nificantly reduced film thickness, with tensile strength values which were on the same order of magnitude as the corresponding values for the non-stress-softened samples, and with tear resistance values which likewise were on the same order of magnitude as the corresponding values for non-stress-softened films. The force required to effect elongation of the stress-softened samples was proportionately much lower than for the corresponding non-stress-softened films.

In general, the stressed-softened films exhibited reduced elongation, as compared to corresponding unstressed films. Concurrently, the fact that the force required to effected elongation was reduced in the stress-softened samples accords with reduced modulus, increased softness, and improved performance properties, relative to corresponding non-stress-softened film samples.

The same quantitative physical property relationships are apparent from the Samples Groups E and F, as compared to Sample Groups G and H.

Example II

Measurement was made of the KES (Kawabata Evaluation System) Hand Properties and certain thermal properties of each of the five Ellastolan ® 1185 polyurethane film samples disclosed in Table II below. Some description of the test procedures is given below. The KES procedures may also be found in *The Standardization and Analysis of Hand Evaluation*, 2nd Ed. 1980, by S. Kawabata. Some citations are made herein to illustrations in Chapter 4 of that publication.

TABLE II

| | Test Materials | |
|---|---|---|
| Sample | Original Film Thickness | Stress-Softened Film Thickness |
| 1 | 50 | SNSS* |
| 2 | 40 | SNSS* |
| 3 | 25 | SNSS* |
| 4 | 50 | 25 |
| 5 | 50 | 25 |

SNSS* = sample not stress-softened

Test Procedures

For samples #1, #2, and #3, the standard specimen size of 20 cm×20 cm was prepared in two replications and conditioned in the laboratory at approximately 70±2° F. and 65±2%RH. For samples #4 and #5, smaller sample sizes were used and are indicated for each test in the tables of results set out hereinafter. Appropriate conversion calculations were done for samples #4 and #5 as needed for making comparisons with the other three samples.

All measurements were directional and were made in both the machine direction/lengthwise (#1), and in the cross direction (#2) of the sample, except in some tests where small sample size of samples #4 and #5 permitted measuring only in one direction. The direction marked with an arrow is labeled the machine direction (or #1 in the tables of results).

The conditions and instrument settings for the KES testing were similar to those used for testing high sensitivity knit fibers. Preliminary experimentation, however, determined that some adjustments of these conditions were needed for these samples which are not typical textile forms. The adjustments are indicated in descriptions of the tests as they are reported below.

The measurements of film characteristics were obtained from the following series of testing with the KES instruments and procedures:

Shear In shear testing, opposing parallel forces are applied to the sample by the KES-FB1 Tensile-Shear Tester (Kawabata, p. 34–36) until a maximum offset angle of 8° was reached. A tension load of 5 gf/cm was applied to the specimen for the shear testing. Shearing stiffness is the ease with which microdomains of film samples slide against each other resulting in soft/pliable to stiff/rigid structures.
  1) G—shear stiffness, gf/cm. degree (higher G value means greater stiffness/resistance to the shearing movement).
Tensile The tensile test, done on the KES-FB1 Tensile-Shear Tester (p. 28–30), measures the stress/strain parameters at the maximum load of 50 gf/cm. Because of the excessive stretchiness of the sample material, a sample length of 2.5 cm was used in the tensile test.
  2) WT—tensile energy, gf/cm/cm$^2$ (higher WT generally means higher extensibility, but this must be interpreted in conjunction with LT).
  3) RT—extensibility, percent strain at maximum load of 50 gf/cm (100%=completely elastic, 0%=completely inelastic).
Weight 4) W—The sample weight was determined in mass per unit area, oz./sq. yd.
Thickness 5) $T_o$—fabric thickness, mm (thickness at pressure of 0.5 gf/cm$^2$).

Thermal Properties Measurement

The thermal properties measured were $Q_{max}$, and dry and wet heat transfer. The two heat transfer tests were performed in a small environmental chamber at standard atmosphere conditions (21° C., 65% RH).

1. $Q_{max}$ (W/M$^{2°}$ C.)

The human cutaneous sensation of warm/cool feeling when coming in contact with a sample surface was measured with a Temperature-box (heat source device) containing a 3 cm.×3 cm. (9 sq. cm.) thin copper skin simulation plate heated to 32.2° C. (approximately body surface temperature). The sample was placed on a plate of insulator styrofoam and the 32.2° C. Temperature-box was placed on the sample surface. The peak value of the rate of heat flow to the sample surface, which occurs within 0.2 sec., was measured. Larger values of $Q_{max}$ indicate cooler feeling fabrics.

2. Heat Transfer with/without Moisture in Various Environmental Conditions

The heat and moisture transfer properties were analyzed at a standard atmosphere condition (21° C., 65%RH). The thermal analyzing system consisted of two parts: 1) an environmental control chamber and 2) a component to simulate the skin/body.

Environmental Chamber

Tabai ESPEC's Platinous Lucifer Model PL-2G, programmable low temperature and humidity chamber was used to produce artificial environmental conditions. This chamber housed a sub-chamber made from Lucite ® plastic that provided precise control of air velocity. A skin simulating guarded hot plate, (BT box) was placed inside the sub-chamber. The air current impinged vertically on the surface of the guarded hot plate. Air currents were varied from 20 cm/sec.

Simulated Skin Models

Simultaneous heat and moisture transfer was measured using a sweating hot plate featuring four moisture sources supplying water to the heated surface at the rate of 0.077 ml/min per gland. The water flow was controlled using an Isamatec cartridge peristaltic pump while the surface of the hot plate was covered by a highly wettable and dimensionally stable polyester/rayon-spunlace nonwoven membrane to allow water to easily spread over the surface. Two simulated skin-contact models were used, including a dry condition and a wet condition. For the dry model, a guarded hot plate was used as a heat source and the specimen was placed directly on it. For the wet model, the moist hot plate was used instead of the guarded hot plate. The skin simulating plate was at 35° C. for both the dry and wet tests.

Analytically, $Q_{max}$ is defined as the peak value of the rate of flow of heat from the heat capacitor to the surface of a film specimen from the moment the capacitor and surface come into contact. This transient response is similar to that occurring as heat is transferred from the surface of the human skin to heat sensitive nerves just beneath the skin. $Q_{max}$ can thus be used as a measure of the warmth or coolness of a film surface.

Q is defined as the heat dissipated from the hot plate through a specimen to air and is a measure of the thermal insulation properties of the material. For its measurement, the hot plate is placed in the wind tunnel through which is blown air of known temperature and humidity at a standard air velocity of 20 cm/s. Thus, a controlled environment is maintained around the specimen. In the Dry Method (DM), a specimen is placed on the hot plate and the rate of heat loss of the hot plate measured. The heat loss using the DM is given the symbol $Q_D$. In the Wet Method (WM), a sweating hot plate is used containing four moisture sources with a peristaltic pump used to control water flow. A highly wettable dimensionally stable polyester-rayon nonwoven membrane is placed on the hot sweating plate and the test specimen is positioned on top thereof. The rate of heat loss of the hot plate $Q_w$ is then measured. The wet membrane is meant to simulate human skin. It should be noted that the measurement of heat dissipation includes the latent vaporization of water. The rate of the water dissipation through the specimen can be obtained approximately from $(Q_w-Q_D)a$, where a is the latent heat of vaporization of the water. The Wet/Space Method (WSM): In this method, the membrane wetted by simulated sweat glands (moisture sources), as described in the Wet Method (above), is postioned on the hot plate and the specimen is placed on top of the membrane with a space created between them. The rate of heat loss of the plate $Q_{WS}$ is then measured. The Dry/Space Method (DSM): In this method, a specimen positioned on top of the hot plate leaving a space between specimen and the surface of the hot plate. The rate of heat loss of the plate $Q_{DS}$ is then measured. This provides a method of determining the rate of water dissipation in the Wet/Space measurement, $(Q_{WS}-Q_{DS})/a$ K is defined as the heat conductivity (measured in units of watts/cm° C.) and can be measured by either the transient method using the heat capacitor or the steady heat flow method using the insulated hot plate and the water-box. In the first method, K is obtained from the slope of the decrease of temperature of the heat capacitor. For the second method, a specimen is placed between the surface of the water-box and the hot plate. The temperature of the hot plate is set at a constant value higher than that of the water-box. The heat loss from the hot plate is then measured. Then $K=Q \cdot D/\Delta T$, where $\Delta T$ is temperature difference between the hot plate and the water-box, D is the thickness of the specimen and Q is the heat loss by the hot plate. This heat loss is indicated directly on a digital meter and also as an output voltage signal.

Very practical application may be implied from the interpretation of these results. The $Q_{max}$ result, as mentioned, may be used for judging the warm/cool touch sensation felt with initial contact of a material. A large $Q_{max}$ value indicates a faster rate of heat flow resulting in a cooler touch sensation, while the smaller $Q_{max}$ value indicates a slower rate of heat flow resulting in a warmer touch sensation.

The amount of energy/heat conducted (K) and dissipated (Q) through the sample material represents the amount of body heat that may be lost through it in wear. Large dissipation value produce large amounts of heat loss. Low dissipation values indicate little heat loss (or high insulating ability).

Results

Table III contains a summary of the results of KES testing and thermal properties. Detailed data are included in Tables IV–VII. Some comments on the results follow the tables.

TABLE III

Summary of Results

| Sample ID | WT | RT | EMT | W | To | Heat Loss Dry | Heat Loss Wet | 'Q' Max |
|---|---|---|---|---|---|---|---|---|
| Film # 1 | 0.370 | 89.025 | 2.125 | 0.0055 | 0.067 | 15.21 | 20.50 | 18.89 |
| Film # 2 | 0.513 | 89.675 | 2.350 | 0.0042 | 0.056 | 14.83 | 20.78 | 15.93 |
| Film # 3 | 0.765 | 94.750 | 3.150 | 0.0029 | 0.040 | 14.00 | 21.24 | 12.63 |
| Film # 4 | 1.453 | 90.650 | 6.650 | 0.0029 | 0.046 | 19.18 | 24.86 | 11.74 |
| Film # 5 | 2.647 | 87.150 | 10.900 | 0.0026 | 0.040 | 18.68 | 24.43 | 10.59 |

TABLE IV

Comparison of KES Shear Properties (gf/cm. degree)

| Sample ID | | G-1 | G-2 | REMARK |
|---|---|---|---|---|
| Film #1 | 1 | 7.700 | 6.390 | Gage 5 cm, sample width 20 cm |
| | 2 | 7.810 | 7.210 | |
| Average | | 7.278 | | |
| Film #2 | 1 | 5.380 | 4.790 | Gage 5 cm, sample width 20 cm |
| | 2 | 5.050 | 4.930 | |
| Average | | 5.038 | | |
| Film #3 | 1 | 3.330 | 3.000 | Gage 5 cm, sample width 20 cm |
| | 2 | 3.240 | 3.210 | |
| Average | | 3.225 | | |
| Film #4 | 1 | 0.830 | | Gage 5 cm, sample width 7.5 cm |
| | 2 | 0.480 | | Sample size not sufficient |
| Average | | 1.747 | | therefore - average is adjusted for 20 cm sample size |
| Film #5 | 1 | 0.450 | | Gage 5 cm, sample width 7.5 cm |
| | 2 | 0.440 | | Sample size not sufficient |
| Average | | 1.187 | | therefore - average is adjusted for 20 cm sample size |

Note: Sensitivity 2 × 5

TABLE V

Comparison of KES Tensile Properties

| | | WT-1 (gf/cm) | WT-2 (gf/cm) | RT-1 (%) | RT-2 (%) | EMT-1 (%) | EMT-1 (%) | REMARK |
|---|---|---|---|---|---|---|---|---|
| Film #1 | 1 | 0.35 | 0.41 | 112.7 | 75.5 | 2.20 | 2.00 | Gage 2.5 cm, sample width 20 cm |
| | 2 | 0.42 | 0.30 | 96.7 | 71.2 | 2.30 | 2.00 | |
| Average | | 0.370 | | 89.025 | | 2.125 | | |
| Film #2 | 1 | 0.44 | 0.55 | 97.2 | 88.6 | 2.20 | 2.60 | Gage 2.5 cm, sample width 20 cm |
| | 2 | 0.43 | 0.63 | 95.4 | 74.5 | 2.20 | 2.40 | |
| Average | | 0.513 | | 89.675 | | 2.350 | | |
| Film #3 | 1 | 0.75 | 0.78 | 93.3 | 96.5 | 2.90 | 3.40 | Gage 2.5 cm, sample width 20 cm |
| | 2 | 0.73 | 0.80 | 96.5 | 92.7 | 3.00 | 3.30 | |
| Average | | 0.765 | | 94.750 | | 2.150 | | |
| Film #4 | 1 | 1.25 | | 89.9 | | 6.60 | | Gage 2.5 cm, sample width 17 cm |
| | 2 | 1.22 | | 91.4 | | 6.70 | | Sample size not sufficient therefore - |
| Average | | 1.453 | | 90.650 | | 6.650 | | average is adjusted for 20 cm sample size |
| Film #5 | 1 | 2.29 | | 84.7 | | 10.80 | | Gage 2.5 cm, sample width 17 cm |
| | 2 | 2.21 | | 89.6 | | 11.00 | | Sample size not sufficient therefore - |

TABLE V-continued

| | | Comparison of KES Tensile Properties | | | | |
|---|---|---|---|---|---|---|
| WT-1 (gf/cm) | WT-2 (gf/cm) | RT-1 (%) | RT-2 (%) | EMT-1 (%) | EMT-1 (%) | REMARK |
| Average | 2.647 | | 87.150 | | 10.900 | average is adjusted for 20 cm sample size |

Note:
Test conditions are similiar to those for high sensitivity knits testing
Fm = 50 gf/cm
Sensitivity 2 × 5

TABLE VI

Comparison of 'Q' max Values

| Sample ID | | W | 'Q' max (W/m2/0C) | Average 'Q' max (W/m2/0C) |
|---|---|---|---|---|
| Film #1 | 1 | 0.168 | 18.67 | |
| | 2 | 0.169 | 18.78 | 18.89 |
| | 3 | 0.173 | 19.22 | |
| Film #2 | 1 | 0.141 | 15.67 | |
| | 2 | 0.145 | 16.11 | 15.93 |
| | 3 | 0.144 | 16.00 | |
| Film #3 | 1 | 0.115 | 12.78 | |
| | 2 | 0.115 | 12.78 | 12.63 |
| | 3 | 0.111 | 12.33 | |
| Film #4 | 1 | 0.108 | 12.00 | |
| | 2 | 0.106 | 11.78 | 11.74 |
| | 3 | 0.103 | 11.44 | |
| Film #5 | 1 | 0.093 | 10.33 | |
| | 2 | 0.098 | 10.87 | 10.59 |
| | 3 | 0.095 | 10.560 | |

Note:
Air temp. = 22.2 degree centigrade
Plate temp. = 32.2 degree centigrade
RH - 65%

TABLE VII

Comparison of Heat Loss

| | | Dry Condition | | | Wet Condition | | |
|---|---|---|---|---|---|---|---|
| | | W | W/m2/0C | Average loss | W | W/m2/0C | Average loss |
| Film #1 | 1 | 2.130 | 15.210 | | 2.88 | 20.57 | |
| | 2 | 2.170 | 15.500 | 15.21 | 2.84 | 20.29 | 20.50 |
| | 3 | 2.090 | 14.930 | | 2.89 | 20.64 | |
| Film #2 | 1 | 2.090 | 14.930 | | 2.88 | 20.57 | |
| | 2 | 2.030 | 14.500 | 14.83 | 2.96 | 21.14 | 20.78 |
| | 3 | 2.110 | 15.070 | | 2.89 | 20.64 | |
| Film #3 | 1 | 2.060 | 14.710 | | 3.02 | 21.57 | |
| | 2 | 1.930 | 13.790 | 14.00 | 2.94 | 21.00 | 21.24 |
| | 3 | 1.890 | 13.500 | | 2.96 | 21.14 | |
| Film #4 | 1 | 2.500 | 17.860 | | 3.51 | 25.07 | |
| | 2 | 2.870 | 20.500 | 19.18 | 3.45 | 24.64 | 24.86 |
| Film #5 | 1 | 2.640 | 18.86 | | 3.41 | 24.36 | |
| | 2 | 2.590 | 18.500 | 18.68 | 3.43 | 24.50 | 24.43 |

Note:
Air Temp. = 21.0 degree centigrade
Plate Temp. = 35.0 degree centigrade
RH % 65
Air velocity 20 cm/sec

Discussion of Results

KES Hand Properties

1. Film #1 was heaviest and films #3, #4, and #5 were lightest and were similar in weight.

2. A measurement of thickness ($T_o$) documents that films #3, #4, and #5 are thinner than films #1 and #2.

3. Results of the shear test provide one of the most significant comparisons of the films for showing softness properties. A comparison of G values shows films #4 and #5, with lower values, have much less stiffness and therefore are more easily sheared. The others have more and varying degrees of stiffness to shearing. Film #1 is the most difficult to shear followed by #2.

4. Analysis of the tensile properties shows some important differences with higher energy loss (WT) for #5 and #4 which is consistent with the measured percent extensibility (EMT). Film #5 has the highest degree of extensibility (10%), or best stretchability property, at maximum load of 50 grams of force. Film #4 is next best with almost 7% extensibility; while films #1 and #2 have much less stretch than #4 and #5.

All films are similar and rather high on resiliency, having about 90% recovery ability. Film #3, at about 95%, shows a little superiority.

Thermal Properties

There is a difference in films for $Q_{max}$, a measure of how rapidly heat is fluxed on initial contact, which determines the degree of "cool feel" that a person senses. Higher values, indicating cooler touch, resulted for films #1 and #2 and film #5 had the lowest value or least cool touch.

2. The measure of heat transfer through the material to the surrounding environment differed with films #4 and #5 having higher heat transfer than other films. They are thinner materials than films #1 and #2 which showed much lower heat transfer ability.

The Kawabata Evaluation System (KES) is used primarily to quantify "hand" in textile assemblies. "Hand is a measure of how a fabric feels. The major properties used to define "hand" are tensile and shear properties.

The pertinent tensile "hand" parameters with respect to condoms are tensile energy (WT) and extensiblity (EMT). The tensile energy is the area under the stress-strain curve, and it relates to the energy which is absorbed by the polymer under a specified stress (50 gf/cm). Generally, the more energy the polymer can absorb, the more extensible it is. According to the KES, the films were ranked (best-to-worst) #5, #4, #3, #2, and #1. Films #4 and #5 were "stress-softened". They were significantly better (2 to 4 times) than film #3 which was of comparable thickness to #4 and #5. Of the five samples evaluated, films #4 and #5 would be the preferred choice for condoms with respect to WT.

$Q_{max}$ values are a transient response of an (almost instantaneous heat flow into a sample; i.e., this is what the nerves in the skin perceive. Higher values of $Q_{max}$ relate to a more cool feel. Considering the current application, a lower value of $Q_{max}$ would be preferable. The $Q_{max}$ values from lowest to highest were for films #5, #4, #3, #2 and #1. The differences in thermal properties are not as dramatic as those in mechanical properties. But they display an improvement with "stress-softening".

The wet and dry heat loss evaluation indicates the ease of heat transfer through the material to the environment. The greater the heat transfer, the more "humanlike" the contact will seem. The highest to lowest dry heat transfer values are for films #4, #5, #1, #2 and #3, and for the wet condition are films #4, #5, #3, #2 and #1. The differences are slight, but they do show that "stress-softening" improves the "thermal feel" of the thermoplastic elastomeric films.

"Stress-softening" makes a significant contribution to the feel mechanical and thermal, of the thermoplastic elastomeric film.

EXAMPLE III

A frontal burst test was carried out on sample tubular articles formed of thermoplastic elastomeric film and having a closed distal end and an open proximal end.

The proximal end of the sample article was circumferentially secured by fixturing of the proximal end in a collar and O-ring assembly on a horizontal base, so that the tubular article depended downwardly from the support structure, with its proximal end opening being in a horizontal plane.

Mounted coaxially above the downwardly hanging tubular article was a hardened stainless steel 0.5-inch diameter shaft six feet in length, and having mounted on its end a miniaturized Entran 50 pound load cell including a stainless steel or brass ball at the lower end thereof, with a diameter of 1.1875-inch or 1.375-inch, depending on the ball employed. The stainless steel shaft was coupled with a 72-inch stroke air over hydraulic cylinder. The sample tubular articles had a 5-inch gauge length, and a diameter of 1.5 inches.

In operation, the stainless steel shaft having the load cell ball assembly at its distal end remained stationary while the condom and support fixture were translated upwardly into the load cell ball assembly until failure (rupture of the tubular article) occurred. The percent elongation to failure was determined for the article.

Set out in Table VII below are initial film thickness and stress-softened film thickness values for sample tubular articles formed of Elastollan ® 1185A polyurethane film, together with the percent elongation to failure values for each sample, and the frontal burst test ratio value for the stress-softened tubular article samples. The frontal burst test ratio is defined as the ratio of the percent elongation to failure value for the stress-softened article, to the corresponding value of a corresponding native (non-stress-softened) article.

TABLE VIII

| Sample | Initial Film Thickness, micrometers | Stress-Softened Film Thickness, micrometers | % Elongation to Failure | Frontal Burst Test Ratio |
|---|---|---|---|---|
| 1A | 50 | SNSS | 140 | — |
| 2A | 50 | 30 | 169 | 1.21 |

TABLE VIII-continued

| Sample | Initial Film Thickness, micrometers | Stress-Softened Film Thickness, micrometers | % Elongation to Failure | Frontal Burst Test Ratio |
|---|---|---|---|---|
| 3A | 50 | 25 | 222 | 1.59 |

SNSS = sample not stress-softened

A corresponding test of tubular articles formed of the same film material as that employed in the tests for Samples 1A–3A, but utilizing a native film thickness of 40 micrometers, and a stress-softened sample whose film thickness was reduced from 40 to 30 micrometers, yielded a corresponding frontal burst test ratio of 1.33.

In general, it is desirable to carry out stress-softening of the tubular article for condom usage, such that the frontal burst test ratio value is from about 1.1 to about 1.8, and more preferably is from about 1.2 to about 1.6.

In this respect, it will be recognized that articles in accordance with the present invention may be formed of a thermoplastic elastomeric film which is initially stress-softened prior to its fabrication into the desired article; alternatively, it may be desirable in some instances to fabricate an article of non-stress-softened thermoplastic elastomeric film, and to subsequently effect stress-softening of the film by treatment of the product article, or a precursor (e.g., partially fabricated) component or sub-structure thereof.

Although the invention has been described with regard to specific aspects, features, and embodiments thereof, it will be recognized that other modifications, variations, and embodiments may readily be utilized, and accordingly, the invention is to be broadly construed to encompass such alternative modifications, variations, and embodiments.

What is claimed is:

1. A stress-softened thermoplastic elastomeric film, having at least one of the following characteristics:
   (i) a shear stiffness value of less than 2.5 gf/cm degree;
   (ii) a tensile energy value of at least 1.0 gf/cm/cm$^2$;
   (iii) an extensibility at 50 gf/cm load of at least 4.0%;
   (iv) a dry heat loss value of at least 16.5 watts/m$^2$/° C.;
   (v) a wet heat loss value of at least 22.0 watts/m$^2$/° C.; and
   (vi) a $Q_{max}$ value of less than 12.25 watts/m$^2$/° C.

2. A stress-softened thermoplastic elastomeric film according to claim 1, characterized by at least one of the following characteristics:
   (i) a film thickness of less than 100 micrometers which has been reduced in thickness by at least 10% from its original film thickness by tensional stretching of the film;
   (ii) an elastic modulus at 20% elongation which is at least 15% lower than the elastic modulus at 20% elongation of a corresponding film of the aforementioned original film thickness, which has not been subjected to such tensional stretching, denoted hereinafter as "native film"; and
   (iii) a break ratio defined by $$\frac{(\% \text{ elongation at break})_{stress\text{-}softened\ film}}{(\% \text{ elongation at break})_{native\ film}},$$

which is less than 0.9 in value.

3. A stress-softened thermoplastic elastomeric film according to claim 2, wherein the relatively harder segments of the polymer are selected from the group consisting of urethane linkages, (meth)acrylate ester moieties, and vinyl arylene groups.

4. A stress-softened thermoplastic elastomeric film according to claim 1, wherein the film is formed of a polymer comprising (i) hydrocarbonaceous chain moieties constituting relatively softer segments of the polymer, and (ii) relatively harder segments of the polymer.

5. A stress-softened thermoplastic elastomeric film according to claim 4, wherein the hydrocarbonaceous chain moieties are derived from polymerizable monomers or precursors, selected from the group consisting of monoolefins, dienes, and polyenes.

6. A stress-softened thermoplastic elastomeric film according to claim 5, wherein the hydrocarbonaceous chain moieties are selected from the group consisting of ethylene, propylene, butylene, butadiene, and isoprene.

7. A stress-softened thermoplastic elastomeric film according to claim 1, wherein the film is formed of a material selected from the group consisting of polyether-based polyurethanes, polyester-based polyurethanes, and multiblock rubber-based copolymers.

8. A stress-softened thermoplastic elastomeric film according to claim 1, wherein the film is formed of a polyether-based polyurethane.

9. A stress-softened thermoplastic elastomeric film according to claim 1, wherein the film is formed of a polyester-based polyurethane.

10. A stress-softened thermoplastic elastomeric film according to claim 1, wherein the film is formed of a multiblock rubber-based copolymer having an A-B-A structure comprising polystyrene end blocks and an elastomeric midblock.

11. A stress-softened thermoplastic elastomeric film according to claim 1, which is of tubular shape having a closed distal end and an open proximal end, and which has been stress-softened by biaxial stretching comprising longitudinal extension thereof under the application of tensional force, concurrently with radial expansion thereof.

12. A film article comprising a stress-softened thermoplastic elastomeric film according to claim 1.

13. A method of stress-softening a thermoplastic elastomeric film comprising tensionally stretching the film by applying thereto a strain which is at least uniaxial in orientation to reduce the thickness of the film by at least 10%, wherein the original thickness of the film is less than 100 micrometers, and such that the film subsequent to such tensional stretching is characterized by: (i) an elastic modulus at 20% elongation which is at least 15% lower than the elastic modulus at 20% elongation of a corresponding film of the same thickness which has not been subjected to the tensional stretching ("native film"); and (ii) at least one of the shear stiffness, tensile energy, extensibility, dry heat loss, wet heat loss, and $Q_{max}$ values, as numerically specified in claim 1.

14. A stress-softened thermoplastic elastomeric film, having at least one of the following characteristics:
(i) a shear stiffness value of from 0.5 to 2.5 gf/cm degree;
(ii) a tensile energy value of from 1 to 3 gf/cm/cm$^2$;
(iii) an extensibility at 50 gf/cm load of 4–12%;
(iv) a dry heat loss value of 16.5 to 20.0 watts/m$^2$/° C.;
(v) a wet heat loss value of 22 to 25 watts/m$^2$/° C.; and
(vi) a $Q_{max}$ value of from 12.25 watts/m$^2$/° C.

* * * * *

UNITED STATES PATENT AND TRADEMARK OFFICE
CERTIFICATE OF CORRECTION

PATENT NO.  : 5,335,675
DATED       : August 9, 1994
INVENTOR(S) : ROBERT G. WHEELER It is certified that error appears in the above-identified patent and that said Letters Patent is hereby corrected as shown below:

On the title page:

Item[75]    "Inventors", the name and address of the second inventor, William D. Hawley, Angier, N.C., In Column 52, Line 34, after "from", the words -- 10 to -- were omitted.

Signed and Sealed this

Eighth Day of November, 1994

Attest:

BRUCE LEHMAN

*Attesting Officer*          *Commissioner of Patents and Trademarks*

UNITED STATES PATENT AND TRADEMARK OFFICE
CERTIFICATE OF CORRECTION

PATENT NO. : 5,335,675
DATED : August 9, 1994
INVENTOR(S) : ROBERT G. WHEELER, ET AL.

It is certified that error appears in the above-identified patent and that said Letters Patent is hereby corrected as shown below:

Before the BACKGROUNG OF THE INVENTION, line 18,
In Column 1, after the title, insert

-- GOVERNMENT LICENSE RIGHTS

The invention claimed herein was made under one or more of the following contracts: U.S. Agency for International Development Contract Nos. DPE-3041-A-00-0043 and DPE-0537-A-00-4047, and National Institutes of Health Contract No. N01-HD-2-3143, and the U.S. government has certain rights therein. --

Signed and Sealed this

Twelfth Day of September, 1995

Attest:

BRUCE LEHMAN

Attesting Officer   Commissioner of Patents and Trademarks

UNITED STATES PATENT AND TRADEMARK OFFICE
CERTIFICATE OF CORRECTION

PATENT NO. : 5,335,675
DATED : August 9, 1994
INVENTOR(S) : Wheeler, Robert G.

It is certified that error appears in the above-indentified patent and that said Letters Patent is hereby corrected as shown below:

Column 1, line 5, insert the following information:

-- <u>GOVERNMENT LICENSE RIGHTS</u>

The invention claimed herein was made under one or more of the following contracts: U.S. Agency for International Development Contract Nos. DPE-3041-A-00-0043 and DPE-0537-A-00-4047, and National Institutes of Heal Contract No. N01-HD-2-3143, and the U.S. Government has certain rights therein. --

Signed and Sealed this

Eighteenth Day of March, 1997

Attest:

BRUCE LEHMAN

*Attesting Officer*  *Commissioner of Patents and Trademarks*